United States Patent
Ginn

(10) Patent No.: US 12,427,027 B2
(45) Date of Patent: Sep. 30, 2025

(54) METHODS FOR SACROILIAC JOINT STABILIZATION

(71) Applicant: Tenon Medical, Inc., Los Gatos, CA (US)

(72) Inventor: Richard S Ginn, Gilroy, CA (US)

(73) Assignee: Tenon Medical, Inc., Los Gatos, CA (US)

( * ) Notice: Subject to any disclaimer, the term of this patent is extended or adjusted under 35 U.S.C. 154(b) by 1065 days.

(21) Appl. No.: 17/463,779

(22) Filed: Sep. 1, 2021

(65) Prior Publication Data

US 2021/0393408 A1  Dec. 23, 2021

Related U.S. Application Data

(63) Continuation-in-part of application No. 13/857,977, filed on Apr. 5, 2013, now Pat. No. 11,273,042, (Continued)

(51) Int. Cl.
  *A61F 2/30* (2006.01)
  *A61B 5/055* (2006.01)
  *A61B 5/06* (2006.01)
  *A61B 6/00* (2006.01)
  *A61B 6/03* (2006.01)
  (Continued)

(52) U.S. Cl.
  CPC .......... *A61F 2/30988* (2013.01); *A61B 5/055* (2013.01); *A61B 5/062* (2013.01); *A61B 6/032* (2013.01); *A61B 6/485* (2013.01); *A61B 8/0841* (2013.01); *A61B 17/1604* (2013.01); *A61B 17/1664* (2013.01); *A61B 17/1671* (2013.01); *A61B 17/70* (2013.01); *A61B 17/7055* (2013.01); *A61B 17/7074* (2013.01); *A61B 17/8858* (2013.01); *A61B 34/20* (2016.02); *A61F 2/4455* (2013.01); *A61F 2/4601* (2013.01); *A61F 2/4611* (2013.01); *A61B 2576/00* (2013.01); *A61F 2002/30121* (2013.01); *A61F 2002/30123* (2013.01);
  (Continued)

(58) Field of Classification Search
  CPC ......... A61F 2002/30995; A61F 2/4455; A61B 17/1671; A61B 17/1757
  See application file for complete search history.

(56) References Cited

U.S. PATENT DOCUMENTS

2012/0283837 A1* 11/2012 Bae .................. A61F 2/447
                                                                623/17.16
2013/0218215 A1*  8/2013 Ginn .................. A61B 6/032
                                                                606/86 A
(Continued)

*Primary Examiner* — Lynnsy M Summitt
(74) *Attorney, Agent, or Firm* — Francis Law Group

(57) ABSTRACT

Methods are described for conducting minimally invasive medical interventions utilizing instruments and assemblies thereof to stabilize and/or fixate a dysfunctional sacroiliac (SI) joint. In one embodiment, a defect creation assembly is advanced from a posterior approach into the SI joint and configured to create pilot SI joint opening; portions of which being disposed in the sacrum and ilium bone structures. After the pilot SI joint opening is created, a prosthesis is press-fit into the pilot SI joint opening, wherein the pilot SI joint opening transitions to a larger post-prosthesis insertion SI joint opening and the prosthesis is securely engaged to the sacrum and ilium bone structures.

7 Claims, 29 Drawing Sheets

Related U.S. Application Data which is a continuation of application No. 13/192,289, filed on Jul. 27, 2011, now abandoned.

(60) Provisional application No. 61/368,233, filed on Jul. 27, 2010.

(51) Int. Cl.
| | | |
|---|---|---|
| *A61B 8/08* | (2006.01) | |
| *A61B 17/16* | (2006.01) | |
| *A61B 17/70* | (2006.01) | |
| *A61B 17/88* | (2006.01) | |
| *A61B 34/20* | (2016.01) | |
| *A61F 2/44* | (2006.01) | |
| *A61F 2/46* | (2006.01) | |

(52) U.S. Cl.
CPC ............... *A61F 2002/30166* (2013.01); *A61F 2002/30593* (2013.01); *A61F 2002/30995* (2013.01)

(56) References Cited

U.S. PATENT DOCUMENTS

| | | | |
|---|---|---|---|
| 2014/0135930 A1* | 5/2014 | Georges | A61F 2/4455 623/17.16 |
| 2018/0050128 A1* | 2/2018 | Gabriele | A61L 26/008 |
| 2018/0325676 A1* | 11/2018 | Donner | A61B 17/1739 |

\* cited by examiner

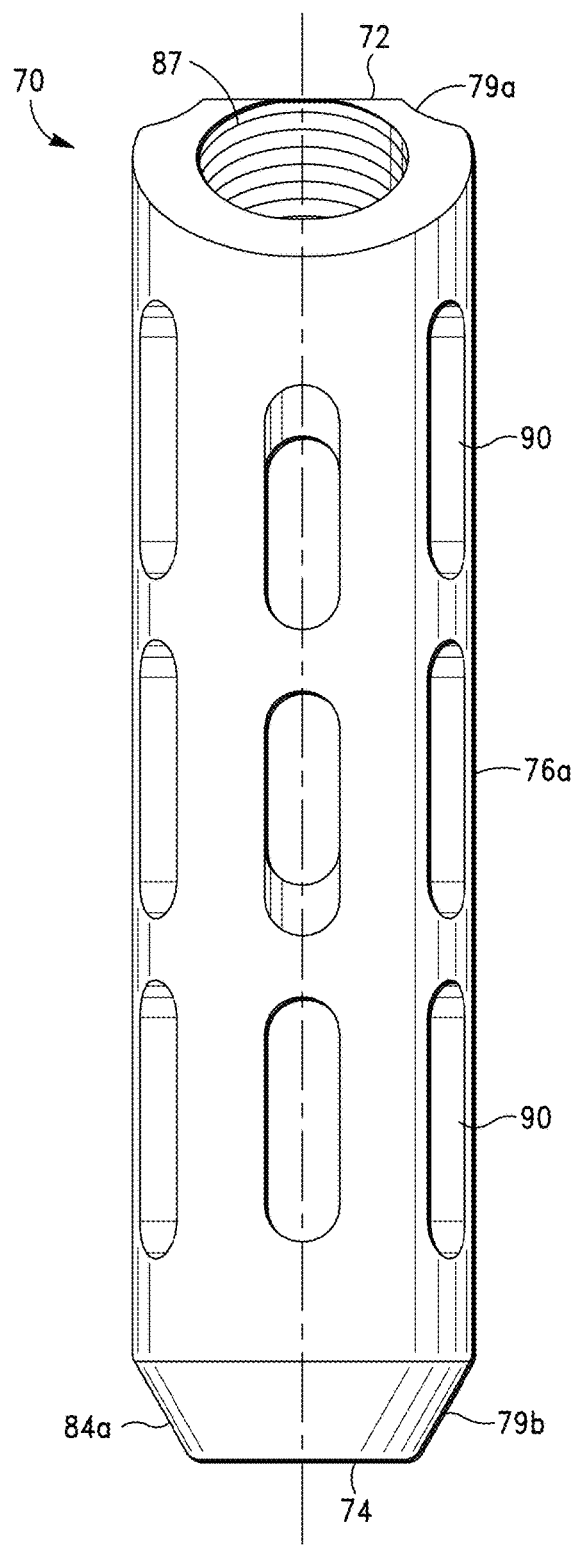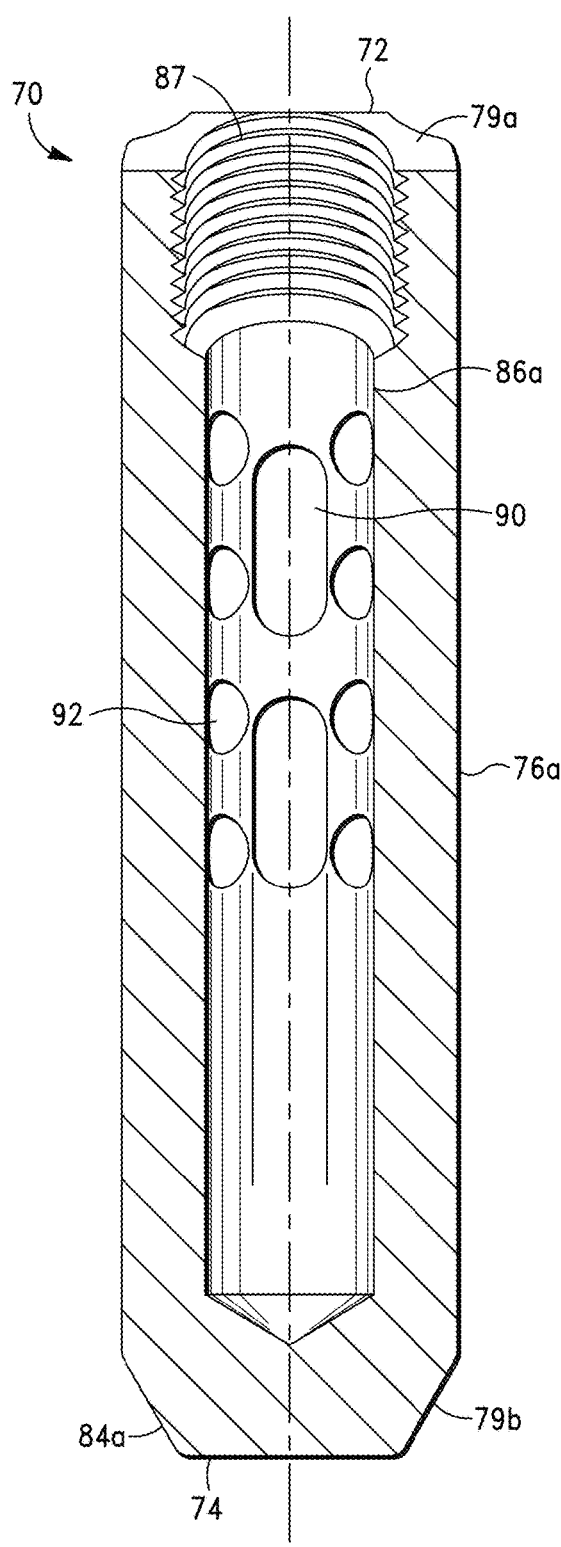
FIG. 6G
FIG. 6H

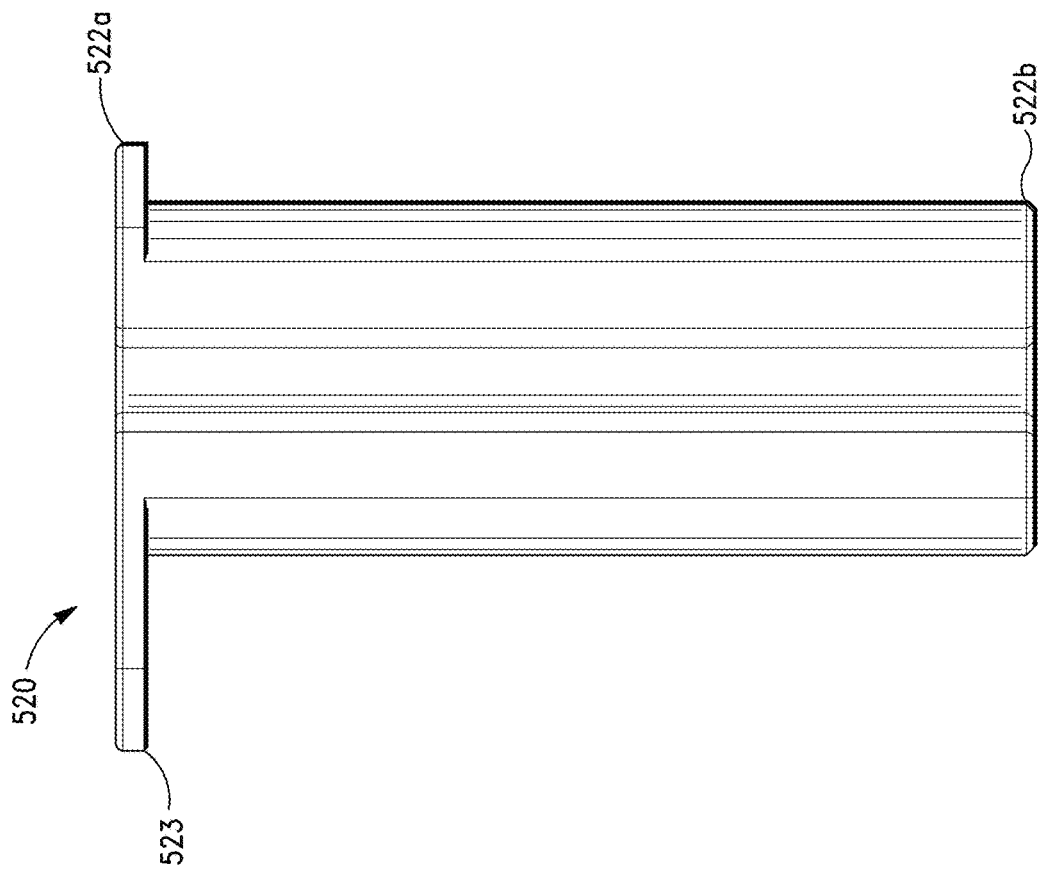
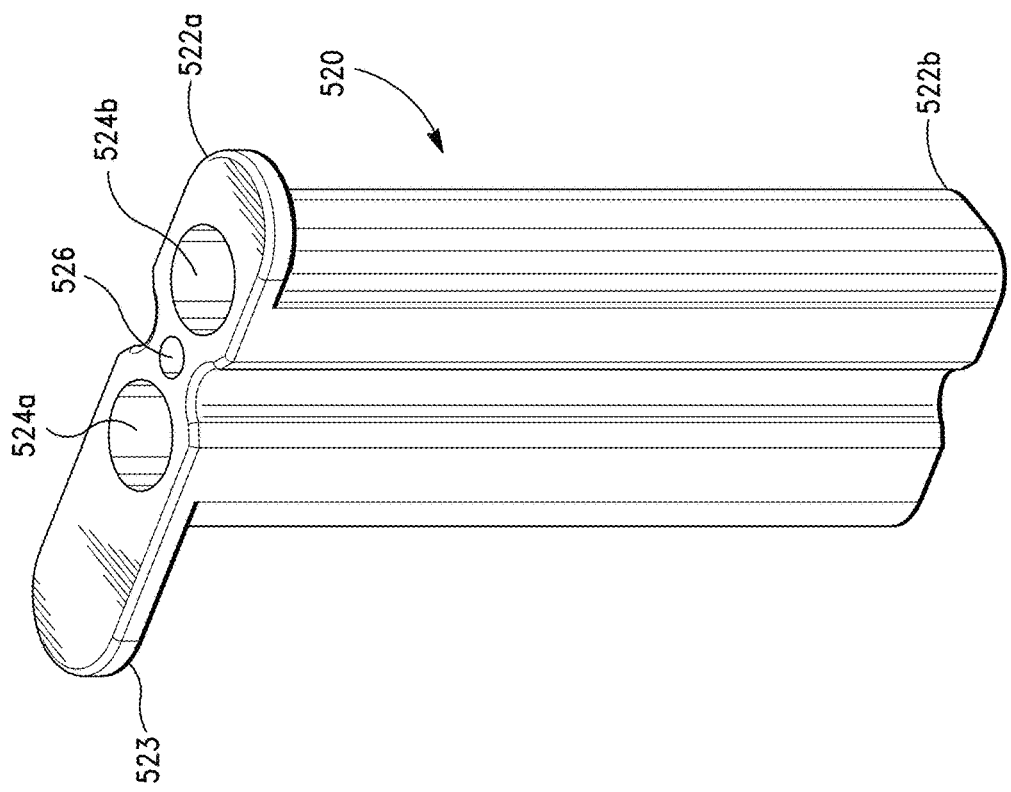
FIG. 9H
FIG. 9G

METHODS FOR SACROILIAC JOINT STABILIZATION

CROSS-REFERENCES TO RELATED APPLICATIONS

This application is a continuation-in-part application of U.S. patent application Ser. No. 13/857,977, filed Apr. 5, 2013, which is a continuation application of U.S. patent application Ser. No. 13/192,289, filed Jul. 27, 2011, now abandoned, which claims the benefit of U.S. provisional patent application Ser. No. 61/368,233, filed Jul. 27, 2010.

FIELD OF THE INVENTION

The present invention relates to methods, systems and apparatus for stabilizing junctions between bone structures. More particularly, the present invention relates to methods, systems and apparatus for stabilizing dysfunctional sacroiliac (SI) joints.

BACKGROUND OF THE INVENTION

As is well known in the art, the sacroiliac (SI) joint 6 comprises a diarthrodial synovial joint, which, as illustrated in FIG. 1A, is defined by the interface between the articular surfaces of the sacrum 2 and the ilium 4. Thus, the SI joint 6 is defined by (and, hence, comprises) portions of the sacrum 2 and ilium 4.

As is also well known in the art, the SI joint further comprises articular cartilage, i.e., hyaline and fibrocartilage, and a strong, extensive ligamentous architecture, which stabilizes the SI joint.

Generally, the articular surfaces of the sacrum 2 and the ilium 4 that define the SI joint 6 comprise cortical bone 8, which is more compact, dense and hard relative to softer trabecular bone 10, which, as further illustrated in FIG. 1A, is disposed in the interior regions of the sacrum and ilium 2, 4.

The SI Joint is distinguished from other synovial joints by the atypical articulation of the different articular surfaces of the sacrum and ilium; the articular surface of the sacrum comprising hyaline cartilage and the articular surface of the ilium comprising substantially stronger fibrocartilage.

As is further well known in the art, the primary plane of motion of the SI joint is anterior-posterior along a transverse axis. The terms often employed to describe the relative motion of the sacrum and ilium are nutation, which refers to anterior-inferior movement of the sacrum while the coccyx (denoted "3" in FIG. 1A) moves posteriorly relative to the ilium, and counternutation, which refers to posterior-superior movement of the sacrum while the coccyx moves anteriorly relative to the ilium.

In most healthy individuals, the SI joint range of motion in flexion-extension is approximately 3°, approximately 1.5° in axial rotation and approximately 0.8° in lateral bending.

As is well established, the SI joint performs several seminal biomechanical functions. The primary functions of the SI joint are to attenuate loads exerted on the upper body and to distribute the loads to the lower extremities. The SI joint also functions as a shock absorber for loads exerted on spine.

As is also well established, the noted loads and, hence, forces exerted on the SI joint can adversely affect the biomechanical functions of the SI joint, which can, and often will, result in SI joint dysfunction—an often-overlooked musculoskeletal pathology associated with lower back pain.

Indeed, SI joint dysfunction is estimated to be the primary cause of lower back pain in 15-30% of subjects afflicted with such pain. However, lower back pain associated with SI joint dysfunction is suspected to be far more common than most healthcare providers realize, since such pain is often associated with other skeletal and musculoskeletal dysfunctions.

SI joint dysfunction, and pain associated therewith, can be caused by various SI joint abnormalities and/or disorders, including traumatic fracture dislocation of the pelvis, degenerative arthritis, sacroiliitis, i.e., an inflammation or degenerative condition of the sacroiliac joint; osteitis condensans ilii, and other degenerative conditions of the SI joint structures.

Various non-surgical methods, such as administration of pharmacological agents, e.g., the corticosteroid prednisone, and surgical methods and devices, i.e., prostheses, have been developed and employed to treat SI joint dysfunction.

The most common approach employed to treat SI joint dysfunctions (when non-surgical treatments fail to ameliorate pain associated therewith), at present, is SI joint stabilization, i.e., reinforcing or modulating articulation by and between the sacrum and ilium, via surgical intervention.

SI joint stabilization typically comprises surgical placement of a prosthesis proximate to or in a dysfunctional SI joint and is generally characterized by the direction of access to the dysfunctional SI joint, i.e., anterior, posterior or lateral.

Although several conventional SI joint stabilization surgical methods and associated bone prostheses have effectively ameliorated pain associated with SI joint dysfunction, there remains many disadvantages associated with the conventional methods and associated prostheses.

A major disadvantage associated with many conventional SI joint stabilization surgical methods is that the surgeon is required to make a substantial incision in and through the skin and tissues of a subject to access the dysfunctional SI joint. Often referred to as "open surgery" methods, these surgical methods have the attendant disadvantages of requiring general anesthesia and often involve increased operative time, pain, hospitalization, and recovery time due to the extensive soft tissue damage. There is also an increased probability of post-surgical complication associated with open surgery methods, such as nosocomial infection.

Minimally-invasive methods for SI joint stabilization have thus been developed to address the noted disadvantages associated with open surgery methods. Although conventional minimally-invasive SI joint stabilization methods, such as the methods disclosed in U.S. Pub. No. 2009/0076551 to Petersen, have garnered some success in relieving pain associated with SI joint dysfunction and have effectively addressed many of the disadvantages associated with open surgery methods, there similarly remains many disadvantages associated with conventional minimally-invasive SI joint stabilization methods.

A major disadvantage associated with many conventional minimally-invasive SI joint stabilization methods is that such methods are difficult to perform and, hence, often require extensive, system-specific surgical training and experience. Despite the level of surgical training and experience that surgeons possess, when such conventional minimally-invasive SI joint stabilization methods are employed, there is still a substantial incidence of damage to the lumbosacral neurovascular structures proximate to the SI joint.

A further disadvantage associated with many conventional minimally-invasive SI joint stabilization methods and associated apparatus, i.e., prostheses, such as the methods and prostheses disclosed in U.S. Pub. No. 2009/0076551 to Petersen, is that pre-existing sacral abnormalities can lead to displacement of the implanted prostheses, which can, and often will result in damage to surrounding bone and soft tissue structures.

An additional disadvantage associated with many conventional minimally invasive SI joint stabilization methods is that they comprise anterior or lateral approaches to the dysfunctional SI joint and, hence, muscles, e.g., gluteal aponeurotic fascia and gluteus medius, and ligaments are typically disrupted, and nerves and blood vessels are susceptible to damage during placement of a prosthesis in a dysfunctional SI joint.

Further, some conventional minimally-invasive SI joint stabilization methods are particularly prone to failure due to displacement of the prostheses in the dysfunctional SI joint and/or failure of the prostheses to effectively engage the SI joint structures, e.g., articular surfaces of the sacrum and/or ilium.

Various "improved" prostheses have thus been developed for use in minimally-invasive SI joint stabilization methods or procedures to effectively engage SI joint structures and maintain engagement thereto during SI joint function.

Although many of the "improved" prostheses, when deployed properly in a dysfunctional SI joint, can, and often will, effectively engage SI joint structures, there remains several disadvantages associated with the prostheses. Illustrative are the prostheses disclosed in U.S. Pat. No. 8,951,254 to Mayer, et al.

The prostheses disclosed in U.S. Pat. No. 8,951,254 comprise or are coated with a liquefiable synthetic polymer that is adapted to liquefy upon administration of mechanical energy, e.g., high frequency vibration, when implanted and re-solidify thereafter to securely engage the SI joint structures, i.e., sacrum and ilium.

A major disadvantage associated with the prostheses disclosed in U.S. Pat. No. 8,951,254 is that the liquefiable synthetic polymers, when re-solidified in situ, are structurally inferior to the osseous or bone tissue of the sacrum and ilium. The fusion sites between the articular surfaces of the sacrum and ilium that define the SI joint are, thus, highly susceptible to structural fatigue and failure, which can, and often will, result in misalignment of the SI joint and ultimately increased pain for the subject.

A further disadvantage associated with the prostheses disclosed in U.S. Pat. No. 8,951,254 is that the synthetic liquefiable synthetic polymers are also substantially immunogenic and will induce an adverse immune response when the prostheses are implanted in a dysfunctional SI joint. As is well established, the adverse immune response can, and often will, prevent healing and osteogenic processes, e.g., remodeling of damaged osseous tissue and regeneration of new osseous tissue.

Additional disadvantages associated with the prostheses disclosed in U.S. Pat. No. 8,951,254 and many other prostheses designed for minimally-invasive SI joint stabilization are that the noted prostheses are difficult to accurately place in optimum positions in a dysfunctional SI joint and, in many instances, lack sufficient structural properties, such as rigidity and/or fatigue resistance, to effectively stabilize the dysfunctional SI joint.

It would thus be desirable to provide SI joint stabilization methods and associated systems and apparatus, which substantially reduce or eliminate the disadvantages associated with conventional SI joint stabilization methods and associated systems and apparatus.

It is therefore an object of the invention to provide improved SI joint stabilization methods and associated systems and apparatus; particularly, prostheses, which substantially reduce or eliminate the disadvantages associated with conventional SI joint stabilization methods and associated systems and apparatus.

It is another object of the invention to provide improved minimally-invasive SI joint stabilization methods and associated systems and apparatus that facilitate posterior placement of prostheses in and, thereby, stabilization of dysfunctional SI joints.

It is another object of the invention to provide improved minimally-invasive SI joint stabilization methods and associated systems and apparatus; particularly, prostheses, that can be readily employed to stabilize dysfunctional SI joints.

It is another object of the invention to provide improved minimally-invasive SI joint stabilization methods and associated systems and apparatus, which effectively ameliorate pain associated with SI joint dysfunction.

It is another object of the invention to provide improved SI joint prostheses that can readily be employed in minimally-invasive SI joint stabilization methods and provide secure engagement to SI joint structures.

It is another object of the invention to provide improved SI joint prostheses that can readily be employed in minimally-invasive SI joint stabilization methods and possess optimal structural properties to effectively stabilize dysfunctional SI joints.

It is yet another object of the invention to provide improved SI joint prostheses that can readily be employed in minimally-invasive SI joint stabilization methods and facilitate remodeling of damaged osseous tissue and regeneration of new osseous tissue and osseous tissue structures.

SUMMARY OF THE INVENTION

The present invention is directed to minimally-invasive methods, systems and apparatus for stabilizing dysfunctional SI joints.

In some embodiments of the invention, there are thus provided minimally-invasive methods for stabilizing dysfunctional SI joints. In one embodiment, the minimally-invasive method generally comprises the steps of:

a. providing a tool assembly adapted to access a dysfunctional SI joint of a subject via a posterior approach, the tool assembly comprising an elongated guide probe, an SI joint opening or defect creation assembly, and prosthesis deployment assembly, the elongated guide probe being adapted to be positioned in the dysfunctional SI joint and, as discussed below, function as a guide for advancing the defect creation assembly into the dysfunctional SI joint and placement of a prosthesis therein, the defect creation assembly being adapted to create a pilot SI joint opening in the dysfunctional SI joint, the defect creation assembly comprising a guide member lumen that extends through the defect creation assembly, the guide member lumen being adapted to receive the guide probe therein to facilitate translation of the defect creation assembly thereon, the defect creation assembly further comprising a bone dislodging member adapted to dislodge portions of bone in the dysfunctional SI joint, the pilot SI joint opening comprising a first portion disposed in the sacrum and comprising a sacrum opening cross-sectional shape, and a second portion disposed in the ilium and comprising an ilium opening cross-sectional shape, the prosthesis deployment assembly comprising prosthesis engagement means;

b. providing a prosthesis comprising first and second elongated partially cylindrical sections connected to a bridge section, whereby the prosthesis comprises a continuous exterior surface comprising first and second partially cylindrical surface regions, the first partially cylindrical surface region comprising a first partially cylindrical surface region cross-sectional shape that corresponds to at least a first portion of the sacrum opening cross-sectional shape, the second partially cylindrical surface region comprising a second partially cylindrical surface region cross-sectional shape that corresponds to at least a first portion of the ilium opening cross-sectional shape, the bridge section distal end comprising a first tapered region configured and adapted to disrupt at least articular cartilage and cortical bone, the first elongated partially cylindrical section of the prosthesis comprising a first internal prosthesis engagement member lumen and the second elongated partially cylindrical section of the prosthesis comprising a second internal prosthesis engagement member lumen, the first and second internal prosthesis engagement member lumens adapted to cooperate with the prosthesis engagement means of the prosthesis deployment assembly, the prosthesis further comprising a plurality of slots in communication with the first and second internal prosthesis engagement member lumens, the prosthesis being sized and adapted to be inserted into the pilot SI joint opening;

c. making an incision through tissue of the subject to provide posterior access to the dysfunctional SI joint of the subject;

d. advancing the elongated guide probe of the tool assembly from a posterior approach in and through the incision and into the dysfunctional joint;

e. inserting the elongated guide probe into the defect creation assembly distal end and into and through the guide member lumen of the defect creation assembly;

f. advancing the defect creation assembly along the elongated guide probe into the dysfunctional SI joint;

g. creating the pilot SI joint opening with the defect creation assembly;

h. retracting the defect creation assembly and the elongated guide probe from the dysfunctional SI joint;

i. connecting the prosthesis deployment assembly to the prosthesis;

j. advancing the prosthesis into the pilot SI joint opening with the prosthesis deployment assembly, wherein the prosthesis is press-fit in the pilot SI joint opening and induces a transition of the pilot SI joint opening to an expanded and, hence, larger post-prosthesis insertion SI joint opening; and k. retracting the prosthesis deployment assembly out of the dysfunctional Si joint.

In some embodiments, the method further comprises placing one of the aforementioned biologically active compositions and/or pharmacological compositions in one or both of the internal prosthesis engagement member lumens of the prosthesis after the prosthesis deployment assembly is retracted out of the dysfunctional SI joint.

In some embodiments of the invention, the prosthesis comprises an outer coating comprising one of the aforementioned biologically active agents or pharmacological agents.

In some embodiments of the invention, the outer coating comprises a poly(glycerol sebacate) (PGS) based composition.

In some embodiments, the PGS based composition comprises one or more of the aforementioned biologically active agents or pharmacological agents.

In some embodiments of the invention, the method further comprises the steps of (i) providing an image capture apparatus configured and adapted to capture images of at least the elongated guide probe and defect creation assembly when disposed in the body, and, particularly, disposed proximate and in the dysfunctional SI joint, and (ii) capturing images and, hence, positions and orientations of the elongated guide probe and defect creation assembly when disposed in the body, and, particularly, during advancement of the elongated guide probe and defect creation assembly toward and into the dysfunctional SI joint.

In some embodiments, the method further comprises the step of collecting the dislodged bone material after the pilot SI joint opening is created with the defect creation assembly for subsequent use in a biologically active composition of the invention.

According to the invention, suitable image capture apparatus comprise a fluoroscope, a CT system, an ultrasound system, a radiography system, and a magnetic resonance imaging system.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIG. 6G is a right-side plan view of the prosthesis shown in FIG. 6A, in accordance with the invention;

FIG. 6H is a right-side sectional plan view of the prosthesis shown in FIG. 6A, in accordance with the invention;

FIG. 9G is a perspective view the drill guide of the drill guide assembly shown in FIG. 9A, in accordance with the invention;

FIG. 9H is a front plan view of the drill guide shown in FIG. 9G, in accordance with the invention;

DETAILED DESCRIPTION OF THE PREFERRED EMBODIMENT

Figure 1A:
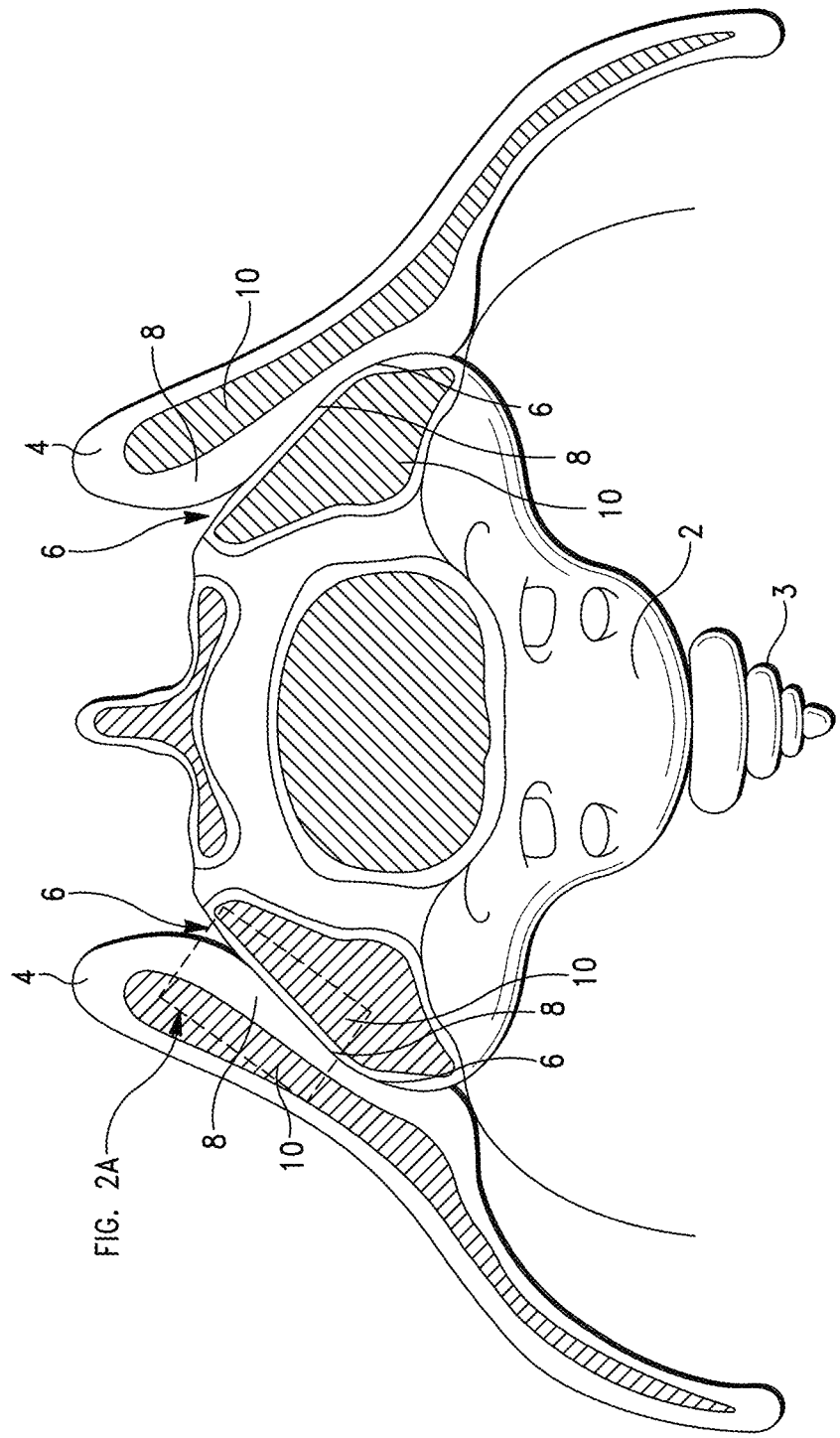
FIG. 1A is a schematic illustration of a human pelvic region from an anteroposterior (AP) perspective showing the SI joints thereof.

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred apparatus, systems, structures and methods are described herein.

It is also to be understood that, although the present invention is described and illustrated in connection with sacroiliac (SI) joint stabilization, fixation and fusion procedures, the invention is not limited to such procedures. According to the invention, the apparatus, systems and methods of the invention can also be employed to stabilize and/or fuse other articulating bone structures, including, without limitation, spinal vertebrae, tarsal bones and the like.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a, "an" and "the" include plural referents unless the content clearly dictates otherwise. Thus, for example, reference to "an incision" includes two or more incisions and the like.

Further, ranges can be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about" or "approximately", it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "about" or "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

Definitions

The terms "sacroiliac joint", "SI joint", "sacroiliac junction" and "SI junction" are used interchangeably herein, and mean and include any region proximate to articulating regions of the sacrum and ilium bone structures and, hence, a junction between and defined by sacrum and ilium bone structures.

The term "dysfunctional" as used in connection with a SI joint, means and includes a physiological abnormality, disorder or impairment of an SI joint, including, but limited to, traumatic fracture dislocation of the pelvis, degenerative arthritis, sacroiliitis, i.e., an inflammation or degenerative condition of the SI joint; osteitis condensans ilii, and other degenerative conditions of SI joint bone structures.

The terms "articular surface" and "articulating surface" are used interchangeably herein in connection with bone structures; particularly, the sacrum and ilium bone structures, and mean and include a surface of a bone structure that forms an articulating junction (i.e., a synovial joint) with an adjacent bone structure, e.g., the articular surfaces of the sacrum and ilium bone structures.

The terms "fusion" and "arthrodesis" are used interchangeably herein in connection with bone structures, and mean and include partial or complete immobilization of adjacent bone structures; particularly, the sacrum and ilium bone structures.

The term "stabilization", as used herein, means and includes reinforcing, e.g., supporting, or modulating motion of adjacent articular bone structures; particularly, the sacrum and ilium bone structures. The term "stabilization", thus, in some instances, means and includes fusion and arthrodesis of adjacent bone structures.

The term "prosthesis", as used herein in connection with bone structures, means and includes a system or apparatus configured and adapted to stabilize or modulate motion of articulating bone structures; particularly, the sacrum and ilium bone structures.

The term "biodegradable", as used herein, means the ability of a material; particularly, a polymer or adhesive, to breakdown and be absorbed within the physiological environment of a SI joint and/or a structure associated therewith, including sacrum and ilium bone structures, by one or more physical, chemical, or cellular processes.

Biodegradable polymers, according to the invention, thus include, without limitation, polylactide polymers (PLA), copolymers of lactic and glycolic acids, including poly (lactic-co-glycolic) acid (PLGA) and poly(ε-caprolactone-co-L-lactic) acid (PCL-LA); glycine/PLA co-polymers, polyethylene oxide (PEO)/PLA block copolymers, acetylated polyvinyl alcohol (PVA)/polycaprolactone copolymers, poly(glycerol sebacate) (PGS) and its derivatives, including poly(glycerol-co-sebacate acrylate) (PGSA); poly (polyol sebacate) (PPS), poly(xylitol sebacate) (PXS), poly (xylitol glutamate sebacate) (PXGS), hydroxybutyrate-hydroxyvalerate copolymers, polyesters such as, but not limited to, aspartic acid and different aliphatic diols; poly (alkylene tartrates) and their copolymers with polyurethanes, polyglutamates with various ester contents and with chemically or enzymatically degradable bonds, other biodegradable nonpeptidic polyamides, amino acid polymers, polyanhydride drug carriers such as, but not limited to, poly(sebacic acid) (PSA); aliphatic-aromatic homopolymers, and poly(anhydride-co-imides), poly(phosphoesters) by matrix or pendant delivery systems, poly(phosphazenes), poly(iminocarbonate), crosslinked poly(ortho ester), hydroxylated polyester-urethanes, or the like.

Biodegradable adhesives, according to the invention, thus include, without limitation, poly(glycerol-co-sebacate acrylate) (PGSA), poly(L-glutamic acid)-based compositions, poly(γ-glutamic acid)-based compositions, poly(alkyl cyano acrylate)-based compositions, polyacrylic acid-based compositions, including polyacrylic acid crosslinked with pentaerythritol and/or allyl sucrose, polyaciylic acid crosslinked with divinyl glycol, and combinations thereof; fibrin-based compositions, collagen-based compositions, including collagen/poly(L-glutamic acid) compositions; albumin-based compositions, including BioGlue® (comprises purified bovine serum albumin (BSA) and glutaraldehyde); cyanoacrylate compositions, including butyl-2-cyanoacrylate adhesives (e.g., Indermil®, Histoacryl®, Histoacryl® Blue, and LiquiBand®) and octyl-2-cyanoacrylate adhesives (e.g., Dermabond®, SurgiSeal™, LiquiBand® Flex, and OctylSeal); poly(ethylene glycol) (PEG) based compositions, including FocalSeal®, Progel™, Duraseal™, DuraSeal™ Xact, Coseal® and ReSure Sealant; polysaccharide-based compositions, polypeptide-based compositions, and combinations thereof.

The term "osteogenic composition", as used herein, means and includes an agent or composition that induces or modulates an osteogenic physiological or biological process, or cellular activity, e.g., induces proliferation, and/or growth and/or remodeling and/or regeneration of bone or osseous tissue.

The term "osteogenic composition" thus means and includes, without limitation, the following osteogenic materials and compositions comprising same: demineralized bone matrix, autograft bone material, allograft bone material, xenograft bone material, polymethyl-methacrylate, calcium-based bone void filler material, including hydroxyapatite (HA) and tricalcium phosphate; and combinations or mixtures thereof.

The term "osteogenic composition" also means and includes, without limitation, the following polymer materials and compositions comprising same: poly(glycerol sebacate) (PGS), poly(glycerol-co-sebacate) acrylate (PGSA) and co-polymers, such as poly(glycerol sebacate)-co-poly (ethylene glycol) (PGS-PEG); and/or composites thereof, e.g., PGS-hydroxyapatite (HA) composites and PGS-poly (ε-caprolactone) (PGS-PCL) composites.

The term "osteogenic composition" also means and includes, without limitation, acellular extracellular matrix (ECM) derived from mammalian tissue sources.

The term "osteogenic composition" thus means and includes, without limitation, acellular ECM derived from bone or osseous tissue, small intestine submucosa (SIS), epithelium of mesodermal origin, i.e., mesothelial tissue, placental tissue, omentum tissue, and combinations thereof.

The terms "biologically active agent" and "biologically active composition" are used interchangeably herein, and mean and include agent or composition that induces or modulates a physiological or biological process, or cellular activity, e.g., induces proliferation, and/or growth and/or regeneration of tissue, including osseous tissue.

The terms "biologically active agent" and "biologically active composition", as used herein, thus include agents and compositions that can be varied in kind or amount to provide a therapeutic level effective to mediate the formation or healing of osseous tissue, cartilage and connective tissue, e.g., tendons and ligaments. The term "biologically active composition", in some instances, thus means and includes an "osteogenic composition."

The terms "biologically active agent" and "biologically active composition" thus mean and include, without limitation, the following bone morphogenic proteins (BMPs) and compositions comprising same: BMP-1, BMP2a, BMP2b, BMP3, BMP4, BMP5, BMP6, BMP7 (also referred to as osteogenic protein 1 (OP-1)) and BMP8a.

The terms "biologically active agent" and "biologically active composition" also mean and include, without limitation, the following biological agents and compositions comprising same: platelet derived growth factor (PDGF), an insulin-like growth factor (IGF), including IGF-1 and IGF-2; basic fibroblast growth factor (bFGF) (also referred to as FGF2), transforming growth factor-β (TGF-β), including, TGF-β1 and TGF-β2; a growth hormone (GH), parathyroid hormone (PTH, including PTH1-34), transforming growth factor-α (TGF-α), granulocyte/macrophage colony stimulating factor (GM-CSF), epidermal growth factor (EGF), growth and differentiation factor-5 (GDF-5), vascular endothelial growth factor (VEGF), angiogenin, angiopoietin-1, del-1, follistatin, granulocyte colony-stimulating factor (G-CSF), hepatocyte growth factor/scatter factor (HGF/SF), interleukin-8 (IL-8), interleukin-10 (IL-10), leptin, midkine, placental growth factor, platelet-derived endothelial cell growth factor (PD-ECGF), platelet-derived growth factor-BB (PDGF-BB), pleiotrophin (PTN), progranulin, proliferin, a matrix metalloproteinase (MMP), angiopoietin 1 (ang1), angiopoietin 2 (ang2) and delta-like ligand 4 (DLL4).

The terms "biologically active agent" and "biologically active composition" also mean and include, without limitation, the following cells and compositions comprising same: bone marrow-derived progenitor cells, bone marrow stromal cells (BMSCs), osteoprogenitor cells, osteoblasts, osteocytes, osteoclasts, committed or partially committed cells from the osteogenic or chondrogenic lineage, hematopoietic stem cells, chondrocytes, chondrogenic progenitor cells (CPCs), mesenchymal stem cells (MSCs) and embryonic stem cells.

The terms "biologically active agent" and "biologically active composition" also mean and include an "extracellular vesicle (EV)", "exosome", "microsome" or "micro-vesicle", which are used interchangeably herein, and mean and include a biological structure formed from a hydrocarbon monolayer or bilayer configured to contain or encase a composition of matter.

The terms "extracellular vesicle (EV)", "exosome", "microsome" and "micro-vesicle" thus include, without limitation, a biological structure formed from a lipid layer configured to contain or encase biologically active agents and/or combinations thereof.

The terms "extracellular vesicle (EV)", "exosome", "microsome" and "micro-vesicle" also include, without limitation, EVs derived from the aforementioned cells and compositions comprising same, e.g., BMSC-derived EVs.

The terms "pharmacological agent" and "active agent" are used interchangeably herein, and mean and include an agent, drug, compound, composition or mixture thereof, including its formulation, which provides some therapeutic, often beneficial, effect. This includes any physiologically or pharmacologically active substance (or composition comprising same) that produces a localized or systemic effect or effects in animals, including warm blooded mammals.

The terms "pharmacological agent" and "active agent" thus mean and include, without limitation, the following osteoinductive agents and compositions comprising same: icaritin, tumor necrosis factor alpha (TNF-α) inhibitors, including etanercept and infliximab, disease-modifying anti-rheumatic drugs (DMARDs), including methotrexate and hydroxychloroquine, antibiotics, anti-viral agents, steroidal anti-inflammatories, non-steroidal anti-inflammatories, anti-thrombotic agents, including anti-coagulants and anti-platelet agents, and vasodilating agents.

The terms "pharmacological agent" and "active agent" further mean and include, without limitation, the following bisphosphonate agents and compositions comprising same: risedronate (Actonel®), alendronate (Fosamax®), ibandronate (Boniva®), zoledronic acid (Reclast®), pamidronate (Aredia®) and etidronate (Didronel®).

The terms "pharmacological agent" and "active agent" further mean and include, without limitation, the following antibiotics and compositions comprising same: penicillin, carboxypenicillins, such as ticarcillin; tetracyclines, such as minocycline; gentamicin, vancomycin, ciprofloxacin, amikacin, aminoglycosides, cephalosporins, clindamycin, erythromycin, fluoroquinolones, macrolides, azolides, metronidazole, trimethoprim-sulfamethoxazole, polymyxin B, oxytetracycline, tobramycin, cefazolin and rifampin.

The terms "anti-inflammatory" and "anti-inflammatory agent" are also used interchangeably herein, and mean and include a "pharmacological agent", which, when a therapeutically effective amount is administered to a subject, prevents or treats bodily tissue inflammation, i.e., the protective tissue response to injury or destruction of tissues, which serves to destroy, dilute, or wall off both the injurious agent and the injured tissues.

Anti-inflammatory agents thus include, without limitation, dexamethasone, betamethasone, prednisone, prednisolone, methylprednisolone sodium succinate, methylprednisolone, cortisone, ketorolac, diclofenac and ibuprofen.

The terms "pharmacological agent" and "active agent" further mean and include, without limitation, the following metal-based antimicrobials and compositions comprising same: silver particles, copper particles, cobalt particles, nickel particles, zinc particles, zirconium particles, molybdenum particles, lead particles and mixtures thereof.

As indicated above, the term "pharmacological composition", as used herein, means and includes a composition comprising a "pharmacological agent" and "active agent".

The term "therapeutically effective", as used herein, means that the amount of the "pharmacological agent" and/or "pharmacological composition" and/or "biologically active agent" and/or "biologically active composition" administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "one embodiment", "one aspect", and "an embodiment" and "an aspect", as used herein, means that a particular feature, structure, or characteristic described in connection with the embodiment may be included in at least one embodiment and not that any particular embodiment is required to have a particular feature, structure or characteristic described herein unless set forth in the claim.

The phrase "in one embodiment" or similar phrases employed herein do not limit the inclusion of a particular element of the invention to a single embodiment. The element may thus be included in other, or all embodiments discussed herein.

The term "substantially", as used herein, means and includes the complete or nearly complete extent or degree of an action, characteristic, property, state, structure, item, or result to function as indicated. For example, an object that is "substantially" enclosed would mean that the object is either completely enclosed or nearly completely enclosed. The exact allowable degree of deviation from absolute completeness may in some cases depend on the specific context, such that enclosing nearly all the length of a lumen would be substantially enclosed, even if the distal end of the structure enclosing the lumen had a slit or channel formed along a portion thereof.

Use of the term "substantially" is equally applicable when used in a negative connotation to refer to the complete or near complete lack of an action, characteristic, property, state, structure, item, or result. For example, structure which is "substantially free of" a bottom would either completely lack a bottom or so nearly completely lack a bottom that the effect would be effectively the same as if it completely lacked a bottom.

The term "comprise" and variations of the term, such as "comprising" and "comprises," means "including, but not limited to" and is not intended to exclude, for example, other components, elements or steps.

The following disclosure is provided to further explain in an enabling fashion the best modes of performing one or more embodiments of the present invention. The disclosure is further offered to enhance the understanding and appreciation for the inventive principles and advantages thereof, rather than to limit in any manner the invention. The invention is defined solely by the appended claims, including any amendments made during the pendency of this application, and all equivalents of those claims as issued.

As indicated above, the present invention is directed to minimally-invasive methods, systems and apparatus for stabilizing dysfunctional SI joints.

In some embodiments of the invention, there are thus provided minimally-invasive methods for stabilizing dysfunctional SI joints. In a preferred embodiment, the minimally-invasive methods (also referred to herein as "minimally-invasive SI joint stabilization methods") comprise a posterior approach to the dysfunctional SI joint.

As indicated above, SI joint stabilization, including minimally-invasive SI joint stabilization, typically comprises surgical placement of a prosthesis proximate to or in a dysfunctional SI joint via anterior, lateral and posterior approaches to the SI joint.

From the perspective of FIG. 1A, an anterior approach to the SI joint 6 (and, hence, a dysfunctional SI joint) would be substantially perpendicular to the page upon which FIG. 1A is printed.

Figure 2A:
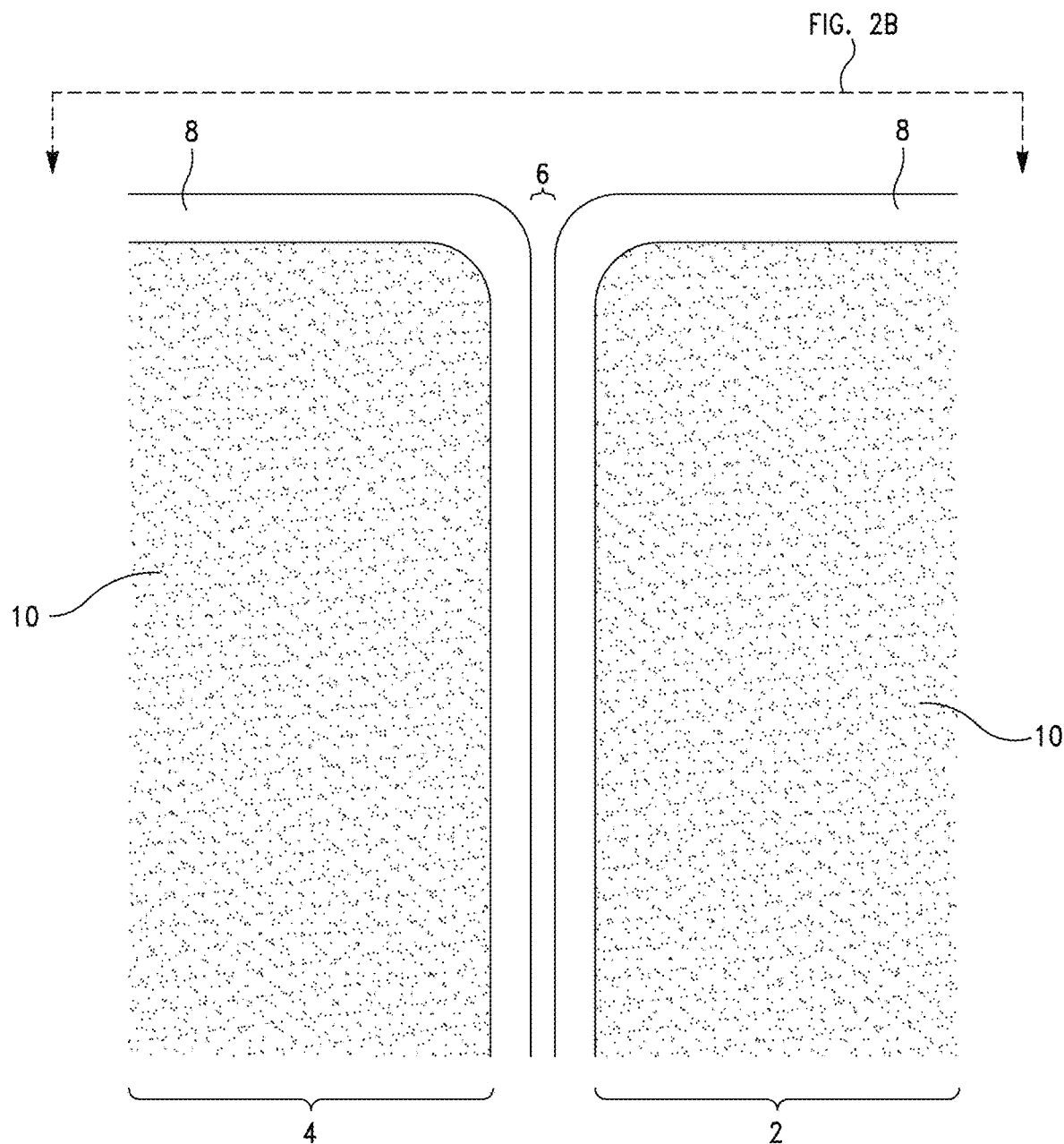
FIG. 2A is an illustration of a SI joint from a superior perspective showing the adjoining sacrum and ilium articular surfaces.

Referring now to FIG. 2A there is shown a close-up illustration of a portion of the leftmost SI joint 6 illustrated in FIG. 1A. For illustrative simplicity, a uniform layer of cortical bone 8 is shown adjacent a deeper layer of trabecular bone 10 on both of the depicted sacrum 2 and ilium 4 portions. However, in actuality, such layers are far less uniform and homogeneous.

Figure 2B:
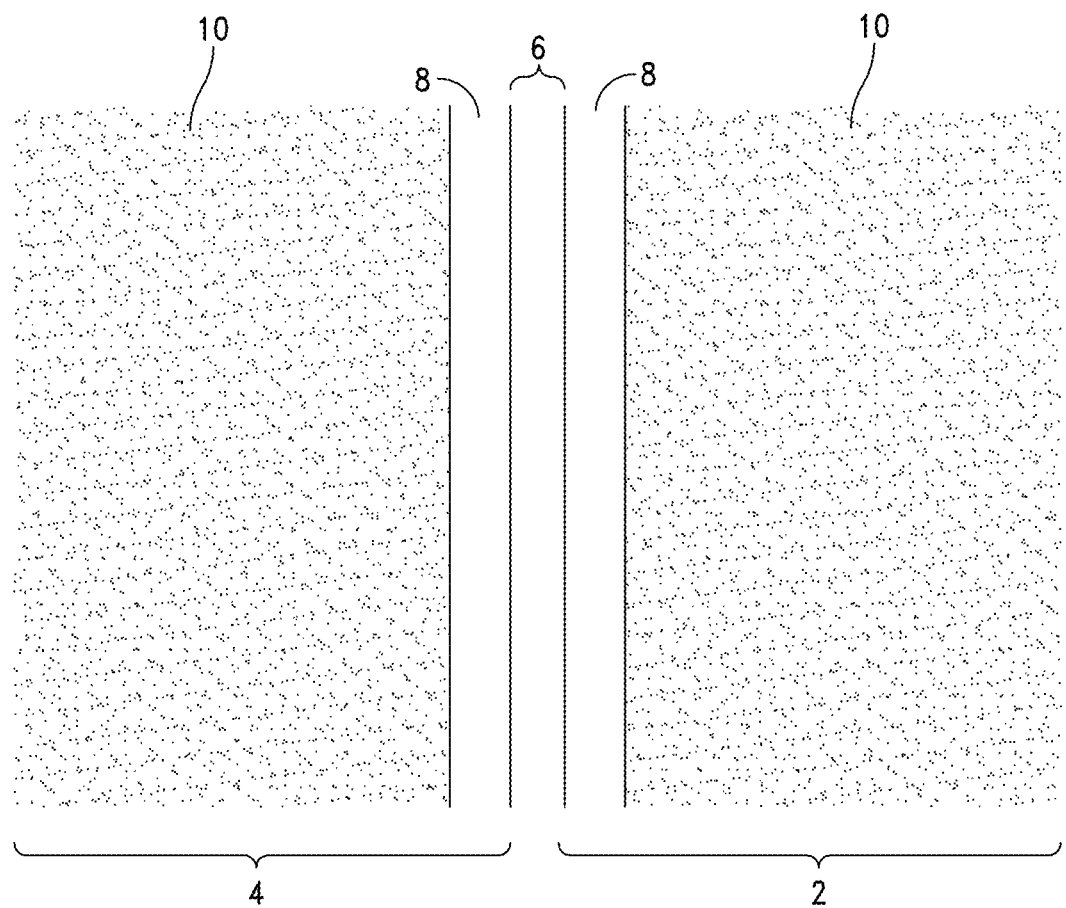
FIG. 2B is another illustration of a SI joint from a posterior perspective showing the adjoining sacrum and ilium articular surfaces.
Figure 2C:
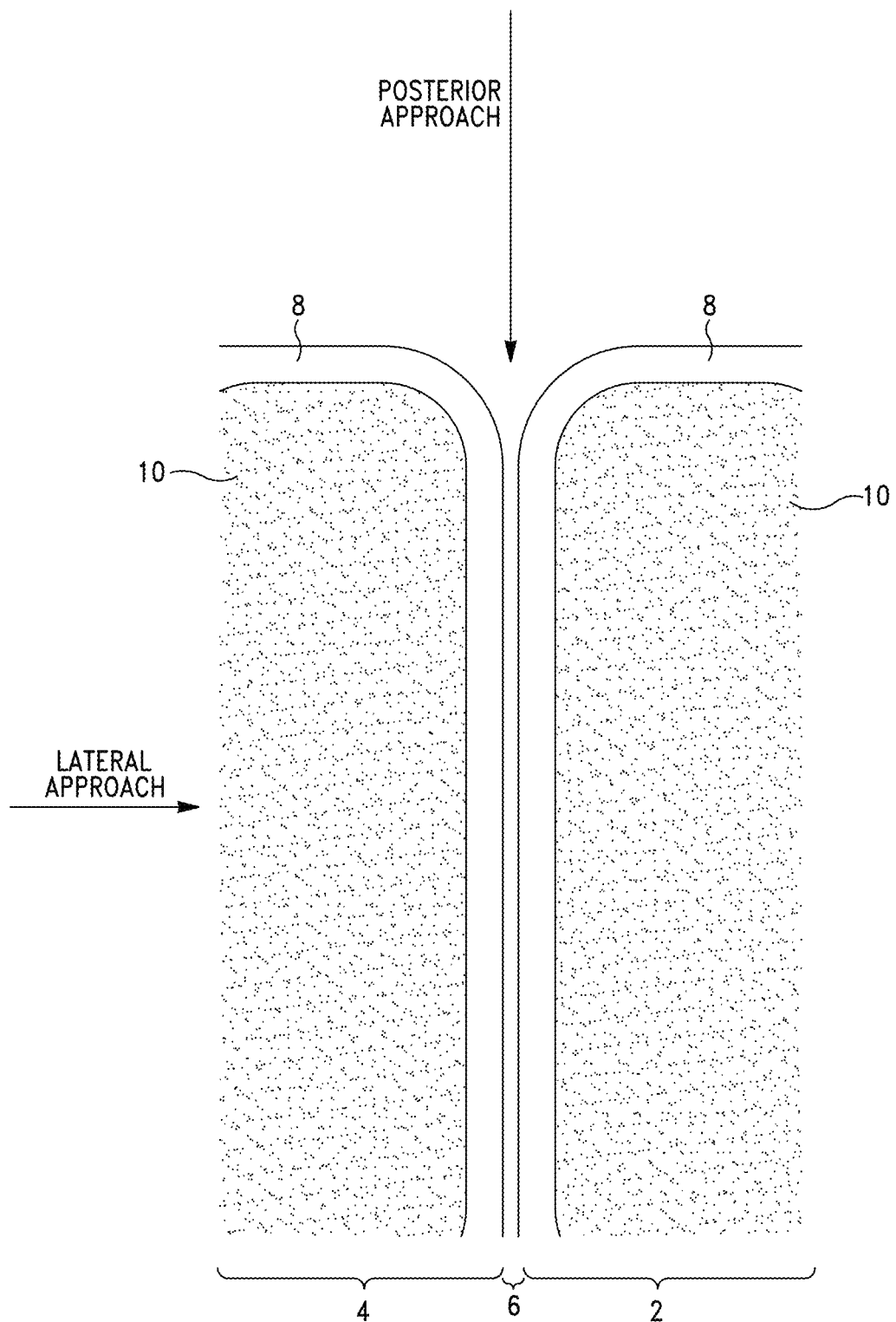
FIG. 2C is a further illustration of the SI joint shown in FIG. 2A showing lateral and posterior approaches to the SI joint, in accordance with the invention.

Referring now to FIG. 2B, there is shown a view of the same structure from a different posterior perspective. From the perspective of FIG. 2B, a posterior approach to the SI joint 6 (and, hence, a dysfunctional SI joint) would be substantially perpendicular to the page upon which FIG. 2B is printed. Indeed, referring to FIG. 2C, a variation similar to that depicted in FIG. 2A is illustrated, showing an approximate approach vector for a lateral approach to the SI joint 6 versus a posterior approach, using the orientation paradigms introduced in FIGS. 1A and 2A-2C. Such paradigm is used to illustrate various embodiments of the subject invention in various figures that follow FIGS. 1A and 2A-2C.

As indicated above, a major disadvantage associated with many conventional anterior or lateral approaches to a dysfunctional SI joint is that muscles and ligaments are typically disrupted and often damaged. Nerves and blood vessels are also susceptible to damage during such SI joint stabilization methods.

In contrast, posterior approaches to a dysfunctional SI joint; particularly, the posterior approach via the minimally-invasive SI joint stabilization methods of the invention described herein, are much less invasive. Indeed, less tissue and fewer muscles are disrupted, and nerves and large blood vessels are avoided.

One of the first steps in the minimally-invasive SI joint stabilization methods of the invention thus comprises providing posterior access; preferably, posterior inferior access to the dysfunctional SI joint. In some embodiments, posterior access to the dysfunctional SI joint is provided by making an incision along the lateral lip of the posterior third of the iliac crest to the posterior superior spine.

Figure 1B:
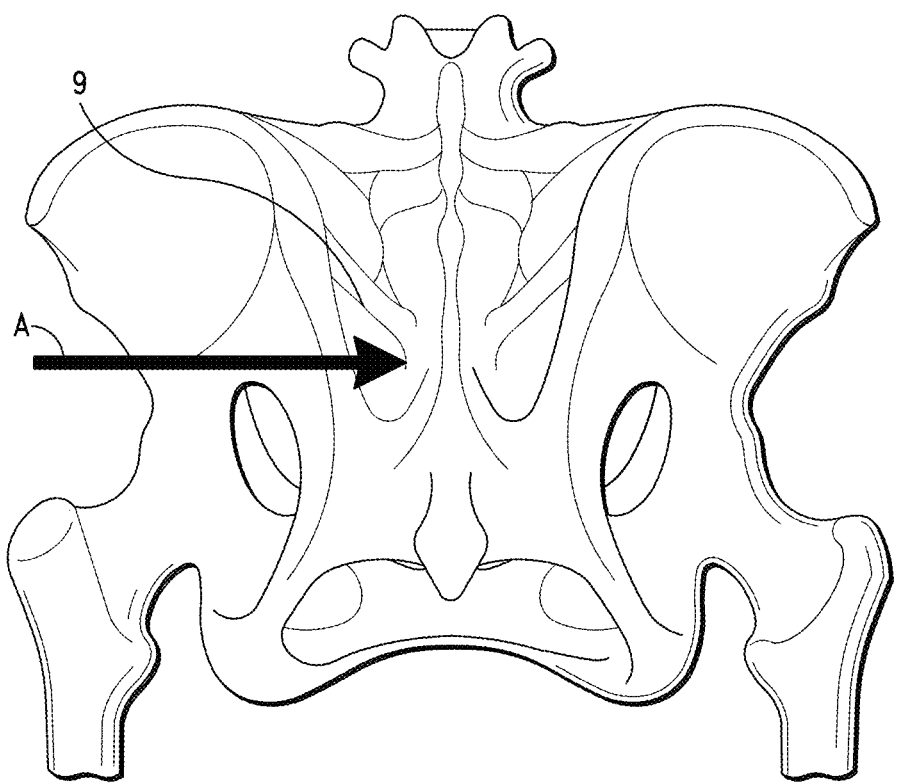
FIG. 1B is another schematic illustration of a human pelvic region from a posterior perspective showing the adjoining sacrum and ilium bone structures, and ligamentous structures thereof.
Figure 1C:
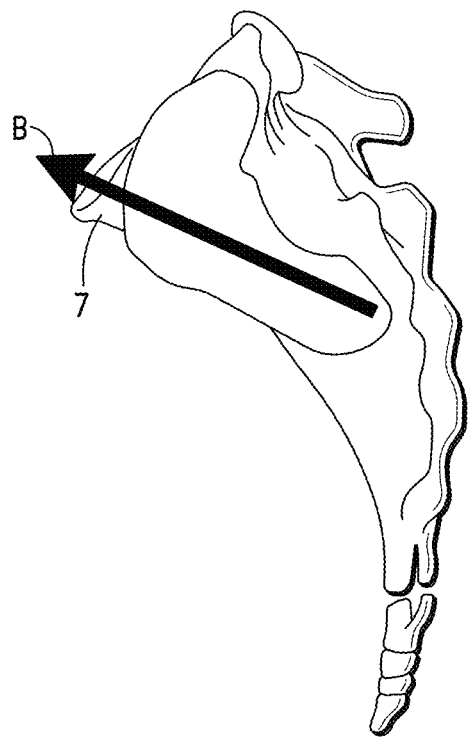
FIG. 1C is a schematic illustration of the sacrum and coccyx from a lateral perspective showing the sacral promontory and the articular surface of sacrum.

Referring to FIG. 1B, in a preferred embodiment, the incision facilitates entry of a prosthesis of the invention into the dysfunctional SI joint through the posterior sacroiliac ligaments 9 at approximately the S3 level (denoted by arrow "A"), and, as illustrated in FIG. 1C, a trajectory of the prosthesis (denoted by arrow "B") toward the mid-point of the S1 end plate and the sacral promontory 7.

A further initial step in the minimally-invasive SI joint stabilization methods of the invention comprises providing a tool assembly configured and adapted to access the target dysfunctional SI joint via a posterior approach.

In a preferred embodiment of the invention, the tool assembly comprises an elongated guide probe, an SI joint opening or defect creation assembly (referred to hereinafter as "defect creation assembly), and prosthesis deployment assembly.

Figure 3A:
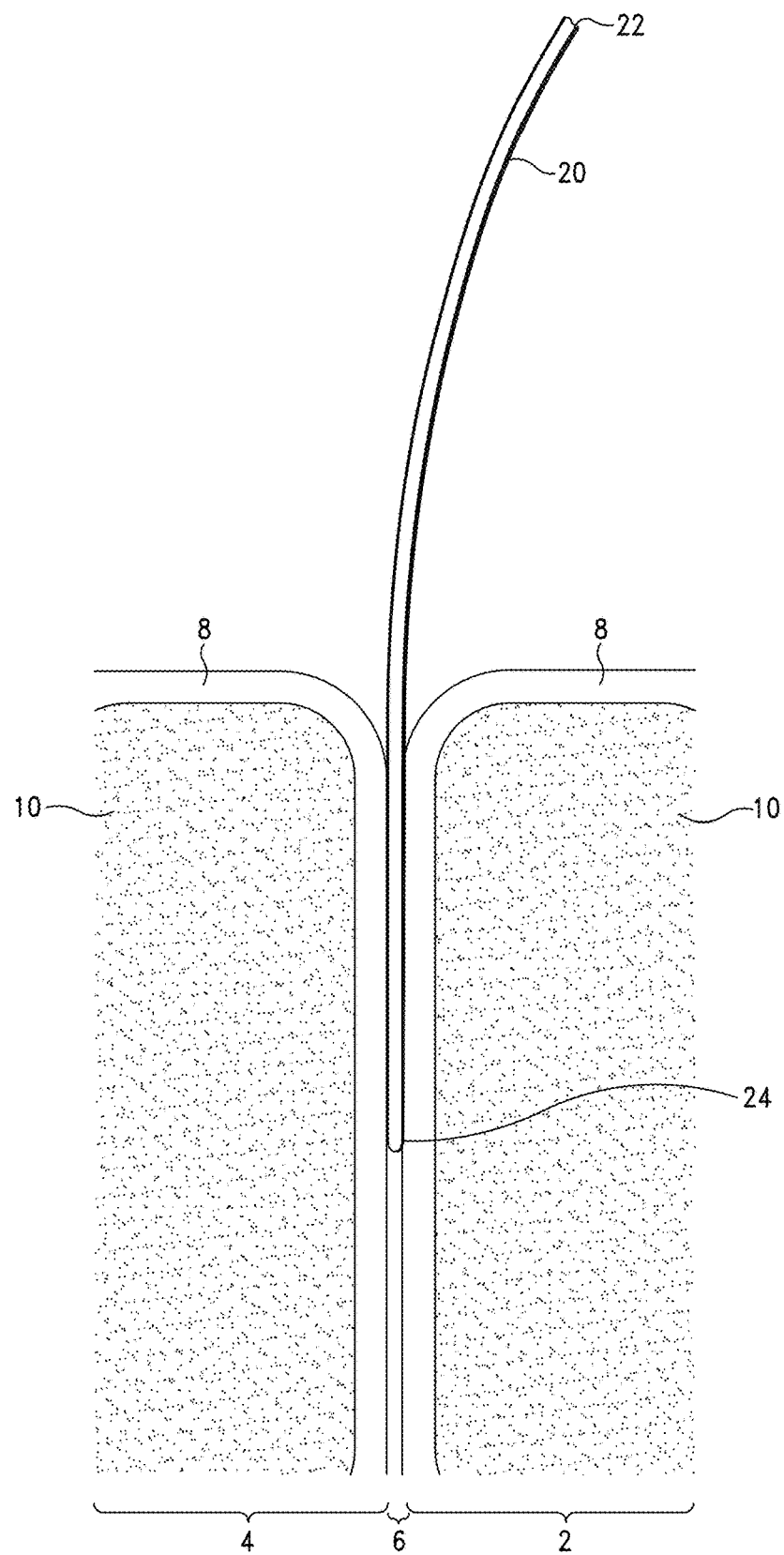
FIG. 3A is a further illustration of the SI joint shown in FIG. 2A showing an elongated guide probe of the invention positioned in the SI joint, in accordance with the invention.

Referring now to FIG. 3A, there is shown a preferred embodiment of elongated guide probe of the invention (denoted "20").

As illustrated in FIG. 3A, the elongated guide probe 20 comprises proximal and distal ends 22, 24, and, as discussed in detail below, is sized and configured to be positioned in the dysfunctional SI joint and function as a guide for advancing the defect creation assembly into the dysfunctional SI joint and placement of a prosthesis therein.

Figure 3B:
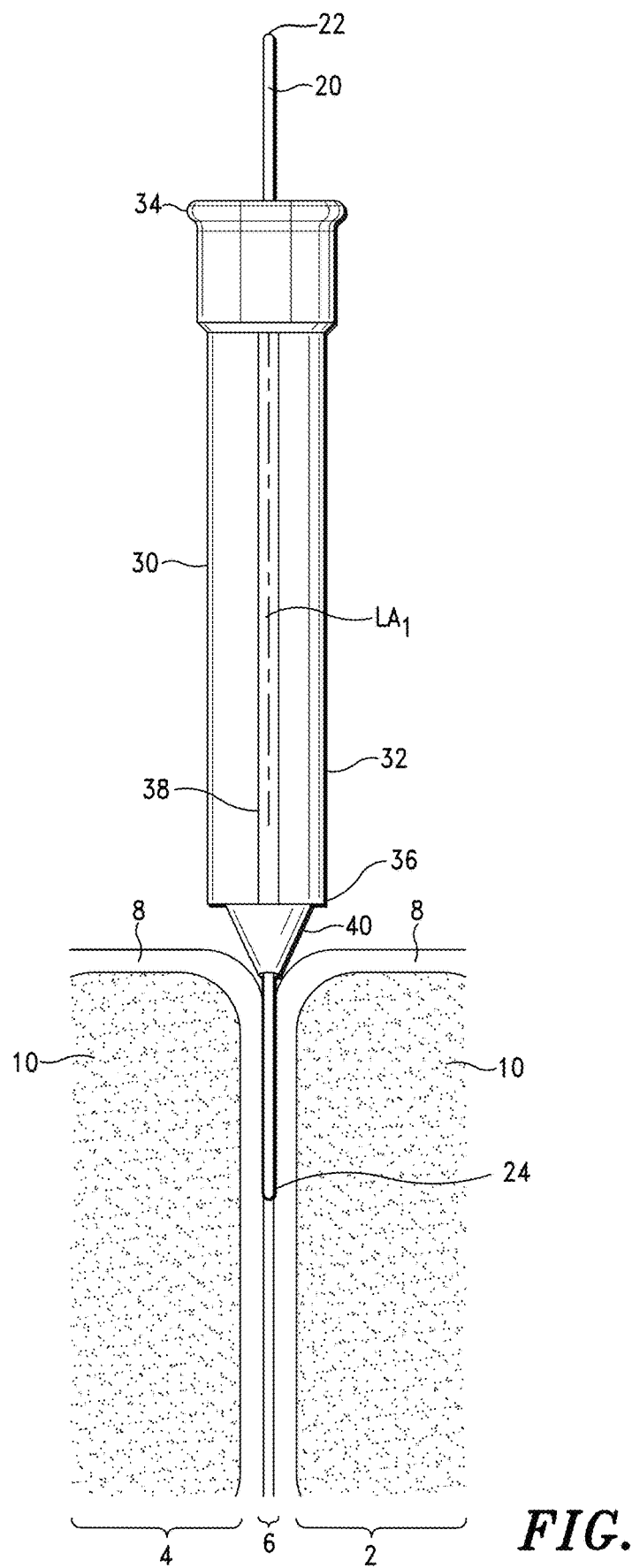
FIG. 3B is a further illustration of the SI joint shown in FIG. 3A showing one embodiment of a defect creation assembly disposed proximate the SI joint, in accordance with the invention.
Figure 3C:
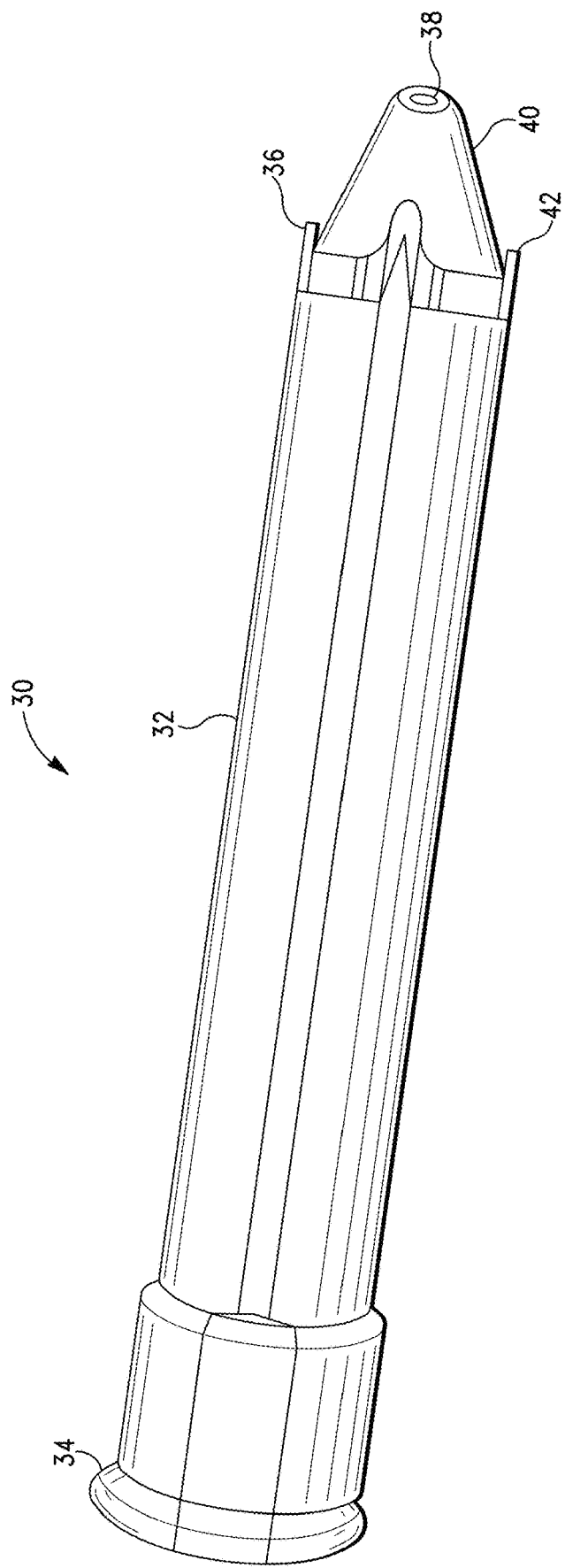
FIG. 3C is a perspective view of the defect creation assembly shown in FIG. 3B, in accordance with the invention.

Referring now to FIGS. 3B and 3C, there is shown one embodiment of a defect creation assembly 30 of the invention (referred to as an "osteotome/cannulation assembly" in Co-pending priority U.S. application Ser. No. 13/857,977).

In a preferred embodiment, the defect creation assembly 30 is configured and adapted to create pre-determined, surgically produced open spaces or defects in the dysfunctional SI joint (referred to herein after as "pilot SI joint openings") to accommodate placement of a prosthesis of the invention therein.

As illustrated in FIGS. 3B and 3C, the defect creation assembly 30 comprises a housing 32, having a longitudinal axis $LA_1$, a proximal end 34, a distal end 36, and a guide member lumen 38 that extends through the defect creation assembly 30. As further illustrated in FIG. 3B, the guide member lumen 38 adapted to receive said guide probe 20 therein, whereby the defect creation assembly 30 is allowed to slidably translate or be advanced along the guide probe 20 to position the joint defect creation assembly 30 proximate to a dysfunctional SI joint site.

In some embodiments of the invention, the defect creation assembly 30 further comprises a bone dislodging apparatus or system 40 disposed on the defect creation assembly distal end 36, which, as also discussed in detail below, is configured and adapted to dislodge portions of bone proximate and in the dysfunctional SI joint.

In some embodiments, the bone dislodging apparatus 40 comprises a bone dislodging tool, such as a drill bit or orthopedic burr, which can be operated manually, pneumatically, or electromechanically. According to the invention, the bone dislodging apparatus 40 can be adapted to communicate with and, thereby, operate with various conventional bone dislodging tools, e.g., a surgical drill.

As shown in greater detail in FIG. 3C, the distal end 36 of the defect creation assembly 30 can also comprise one or more teeth or apices 42 configured to assist with creation of a pilot SI joint opening in SI joint bone structures, i.e., sacrum and ilium bone structures.

As indicated above, in a preferred embodiment, the defect creation assembly 30 is configured and adapted to create pilot SI joint openings in SI joint bone structures to accommodate placement of a prosthesis of the invention therein.

It is however, to be understood that the defect creation assembly 30, described herein, is but one embodiment of a defect creation assembly that can be employed within the scope of the invention to create pilot SI joint openings in SI joint bone structures. Indeed, as indicated above and discussed in detail below, various conventional apparatus and systems, such as a surgical drill, can be employed within the scope of the invention to create pilot SI joint openings of the invention in SI joint bone structures.

As set forth in Co-pending priority application Ser. No. 13/857,977, in some embodiments, a thin layer of cortical bone preferably remains at least in some aspects of a pilot SI joint opening to define the opening volume. In some embodiments, the cortical bone is substantially removed, leaving trabecular bone to substantially define the pilot SI joint opening volume.

As also set forth in Co-pending priority application Ser. No. 13/857,977, the defect creation assemblies of the invention, including defect creation assembly 30, are configured and adapted to create pilot SI joint openings in SI joint bone structures of various sizes and configurations. Illustrative are the pilot SI joint openings depicted in FIGS. 11C-11E of application Ser. No. 13/857,977.

Figure 4A:
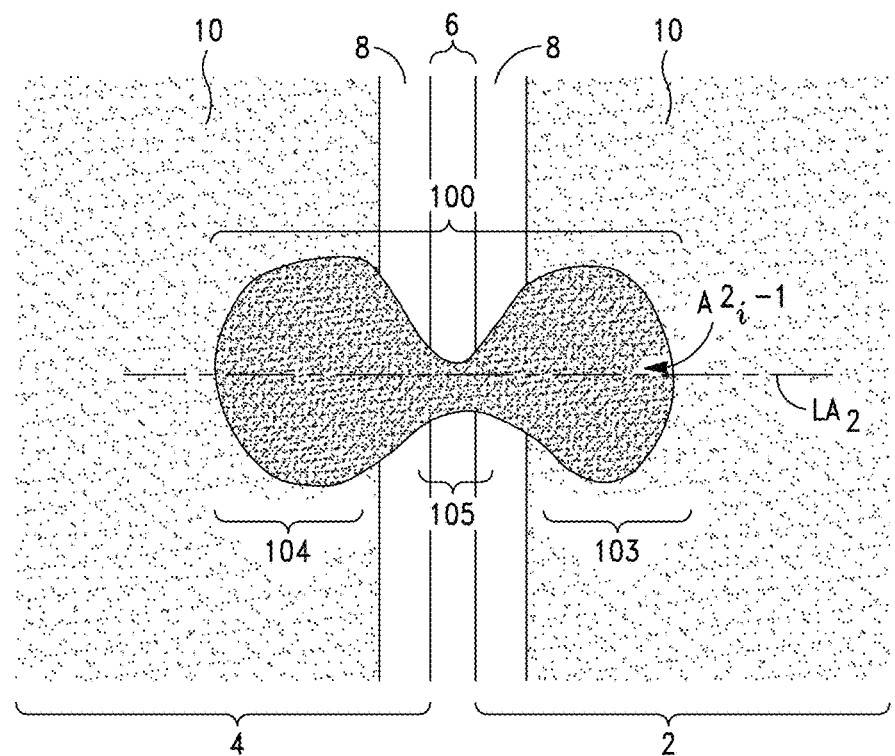
FIG. 4A is a further illustration of the SI joint shown in FIG. 2B showing one embodiment of a pilot SI joint opening, in accordance with the invention.

Referring now to FIG. 4A, there is shown one embodiment of a pilot SI joint opening of the invention (denoted "100") that can be created with the defect creation assemblies of the invention; particularly, defect creation assembly 30.

As illustrated in FIG. 4A, the pilot SI joint opening 100 comprises a three-dimensional opening comprising first and second lobe regions 103, 104; the first lobe region 103 being disposed in the sacrum 2 and comprising a sacrum opening three-dimensional shape, and the second lobe region 104 being disposed in the ilium 4 and comprising an ilium opening three-dimensional shape.

As further illustrated in FIG. 4A, the three-dimensional pilot SI joint opening 100 further comprises an SI joint opening cross-sectional shape in a plane that intersects the sacrum 2 and ilium 4; the plane being substantially perpendicular to the longitudinal axis $LA_1$ of the defect creation assembly 30 when the defect creation assembly 30 is disposed in a defect creation position in the dysfunctional SI joint. The three-dimensional pilot SI joint opening cross-sectional shape thus comprises the sacrum opening three-dimensional shape and ilium opening three-dimensional shape.

In some embodiments, the pilot SI joint opening cross-sectional shape (i.e., pilot SI joint opening 100) is defined in part by at least one noncircular cross-sectional shaped region (denoted "105") in the noted plane.

As additionally illustrated in FIG. 4A, the three-dimensional pilot SI joint opening 100, i.e., cross-sectional shape thereof, also defines a cross-sectional area of the three-dimensional pilot SI joint opening cross-sectional shape (denoted "$A^2_i\text{-}1$")

The three-dimensional pilot SI joint opening 100, i.e., cross-sectional shape thereof, also comprises a longitudinal axis (denoted "$LA_2$") in the plane that intersects the sacrum 2 and ilium 4 and an initial pilot SI joint opening length along the axis $LA_2$.

Figure 4B:
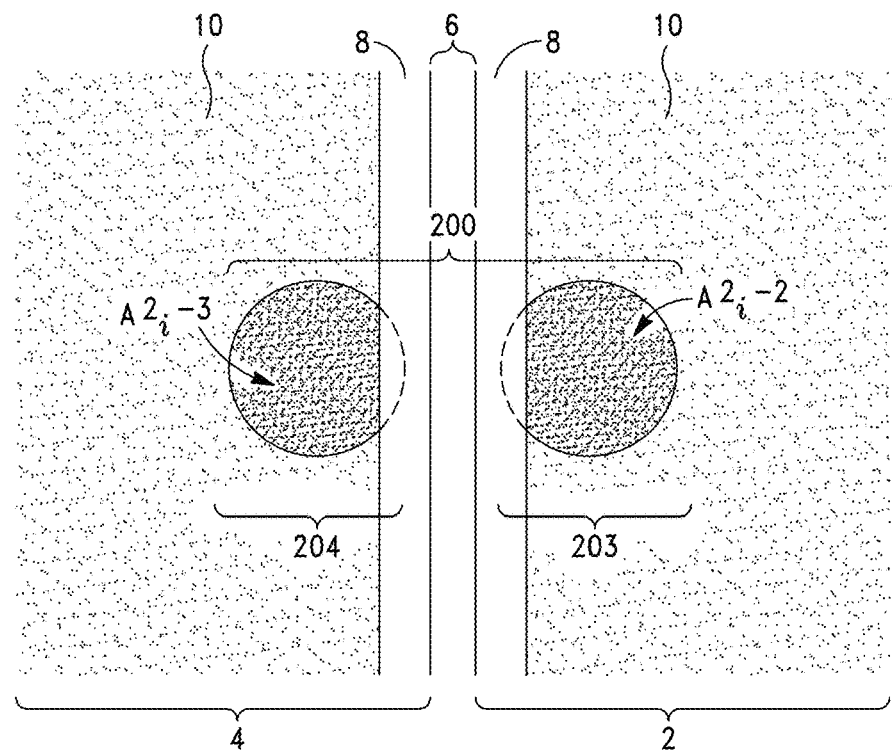
FIGS. 4B and 4C are illustrations of further embodiments of SI joint openings, in accordance with the invention.

Referring now to FIG. 4B, there is shown a further pilot SI joint opening of the invention (denoted "200") that can be created with the defect creation assembly 30 of the invention.

As illustrated in FIG. 4B, the pilot SI joint opening 200 comprises two three-dimensional pilot or guide portions or regions 203, 204; the first guide portion 203 being disposed in the sacrum 2 and the second guide portion 204 being disposed in the ilium 4.

According to the invention, the sacrum and ilium guide portions 203, 204 can comprise various configurations, e.g., cross-sectional shapes, and sizes to, as discussed in detail below, accommodate insertion of defined regions of a prosthesis of the invention therein and transition of the sacrum and ilium guide portions 203, 204 from pilot or first configurations and sizes to expanded second configurations and sizes when the prosthesis is inserted therein.

According to the invention, the sacrum and ilium guide portions 203, 204 can also be disposed at various locations in the sacrum 2 and ilium 4. In some embodiments, the sacrum and ilium guide portions 203, 204 are disposed in the sacrum 2 and ilium 4 such that at least a portion of the sacrum and ilium guide portions 203, 204 extends into the cortical bone 8 of the SI joint structures, i.e., sacrum 2 and ilium 4, as shown in FIG. 4B, or the juncture between the sacrum 2 and ilium 4.

Figure 4C:
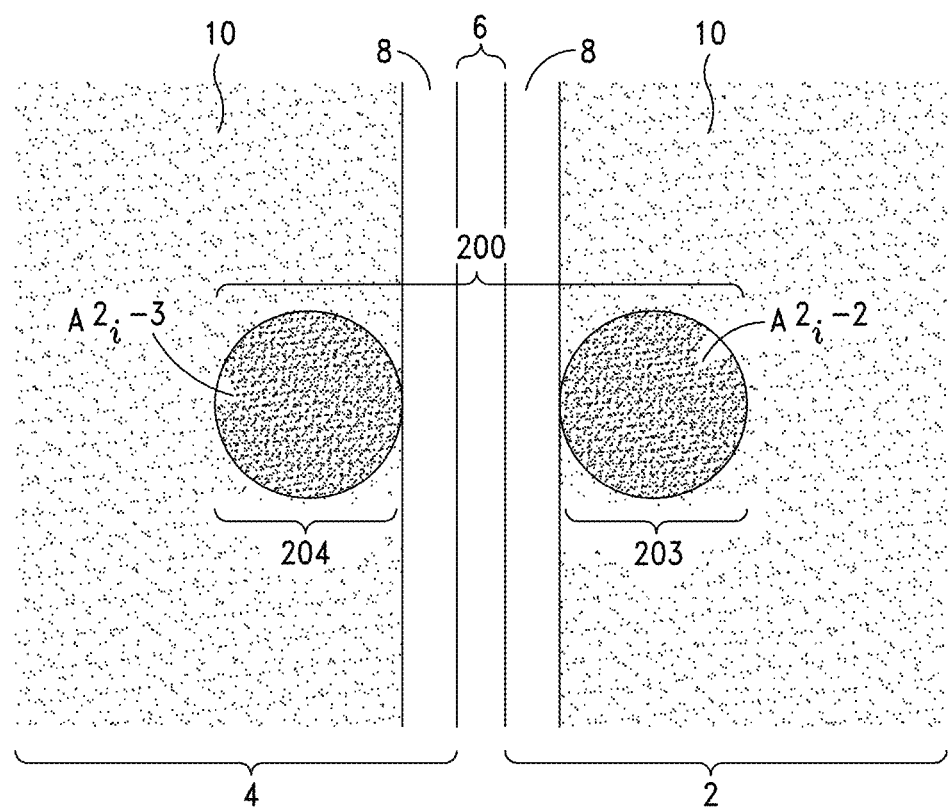

In some embodiments, the sacrum and ilium guide portions 203, 204 are solely disposed in the sacrum 2 and ilium 4, as shown in FIG. 4C.

As illustrated in FIG. 4B, in one preferred embodiment, the sacrum and ilium guide portions 203, 204 comprise substantially circular cross-sectional shapes.

As further illustrated in FIG. 4B, the sacrum and ilium guide portions 203, 204 of the pilot SI joint opening 200, i.e., cross-sectional shape thereof, define cross-sectional areas of the sacrum and ilium guide portions 203, 204 (denoted "$A_i^2$-2" and "$A_i^2$-3", respectively).

In a preferred embodiment, the sacrum and ilium guide portions 203, 204 of the pilot SI joint opening 200 are disposed on a plane that similarly intersects the sacrum 2 and ilium 4.

Figure 5A:
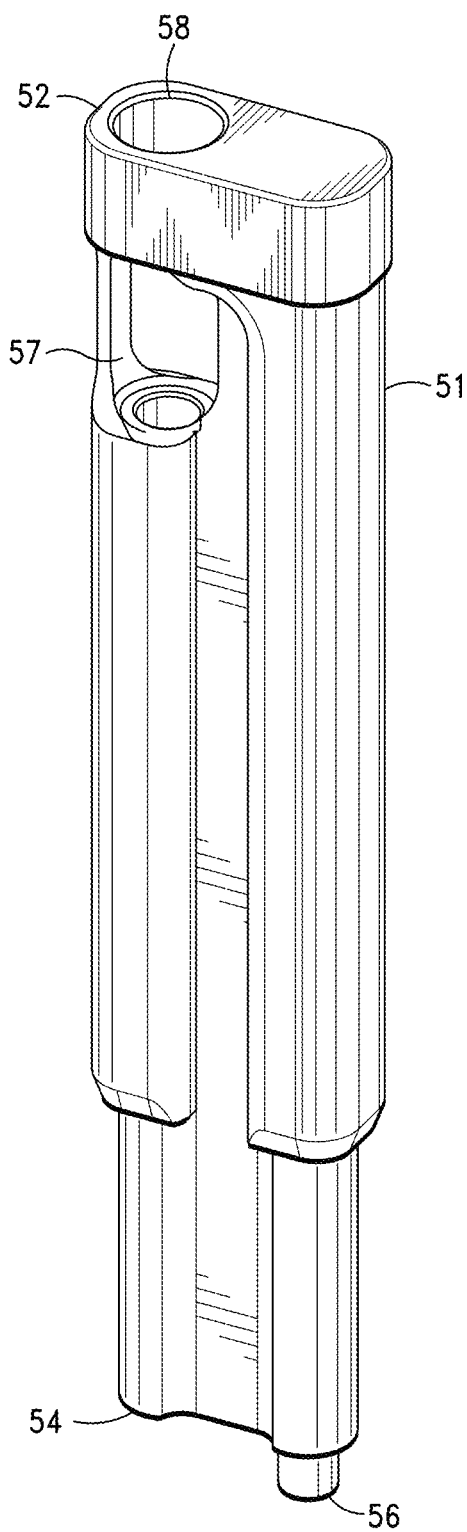
FIG. 5A is a perspective view of one embodiment of a prosthesis deployment assembly, in accordance with the invention.
Figure 5B:
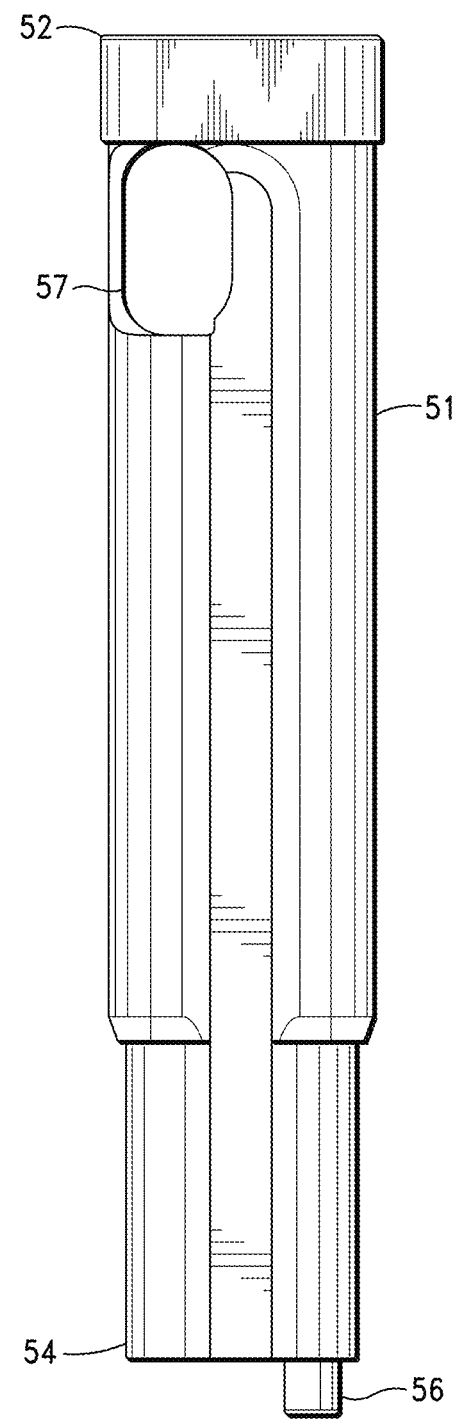
FIG. 5B is a front plan view of the prosthesis deployment assembly shown in FIG. 5A, in accordance with the invention.
Figures 5C, 5D, 5E:
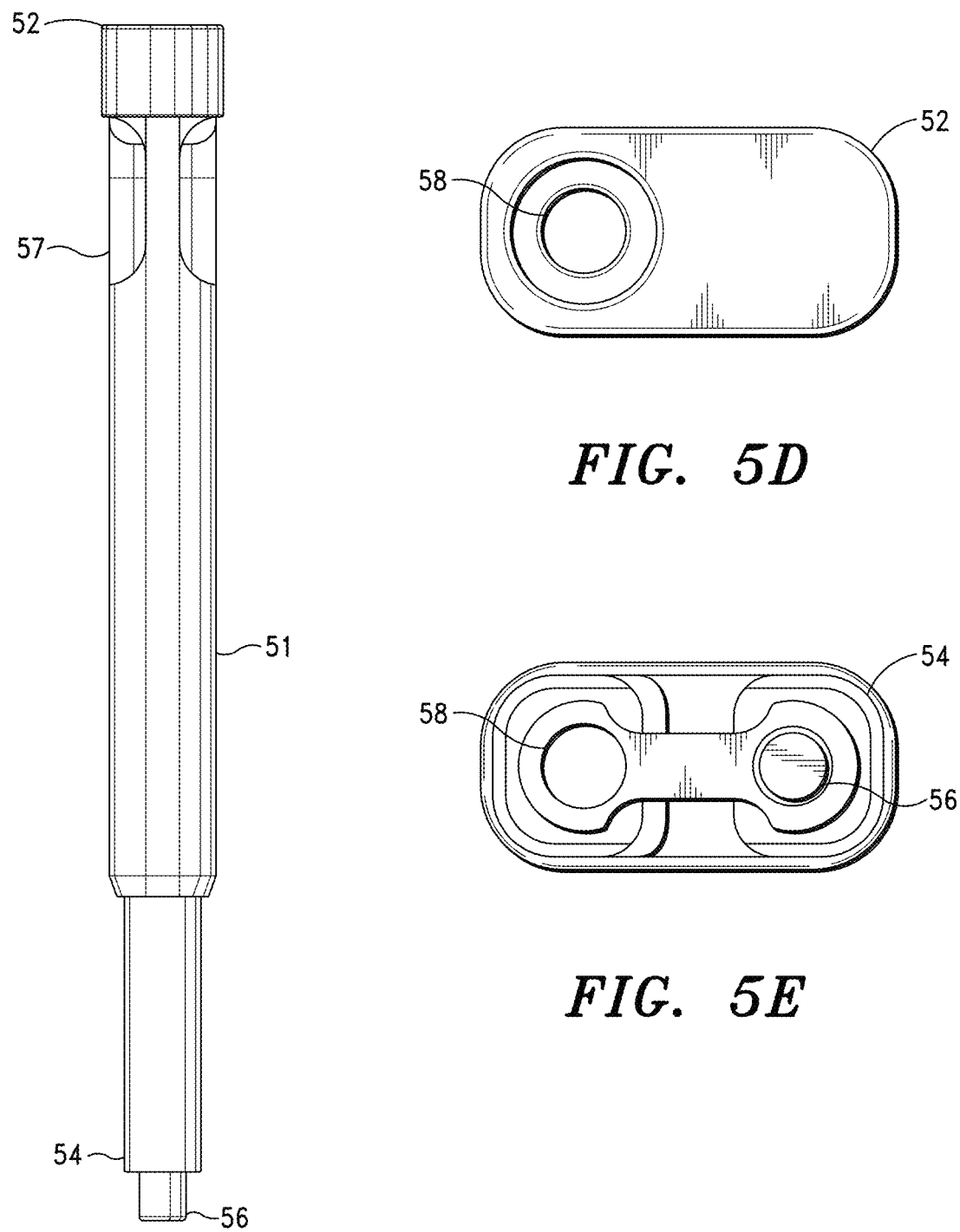
FIG. 5C is a left side plan view of the prosthesis deployment assembly shown in FIG. 5A, in accordance with the invention.
FIG. 5D is a top plan view of the prosthesis deployment assembly shown in FIG. 5A, in accordance with the invention.
FIG. 5E is a bottom plan view of the prosthesis deployment assembly shown in FIG. 5A, in accordance with the invention.
Figure 5F:
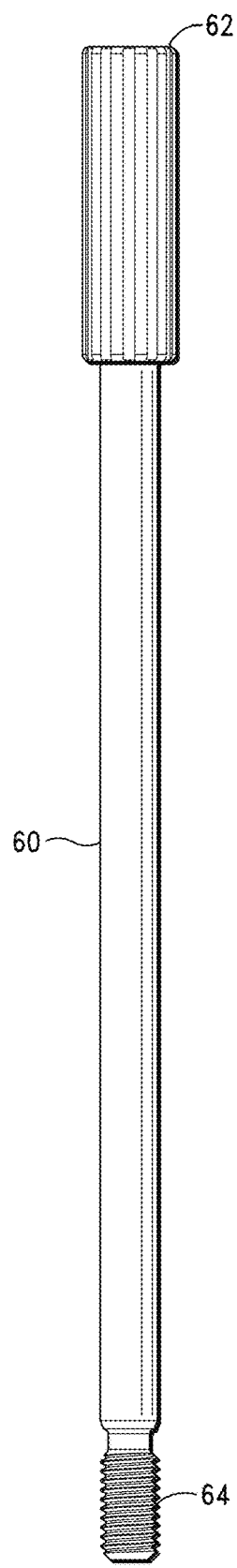
FIG. 5F is a front plan view of a prosthesis engagement rod of the prosthesis deployment assembly shown in FIG. 5A, in accordance with the invention.
Figure 5G:
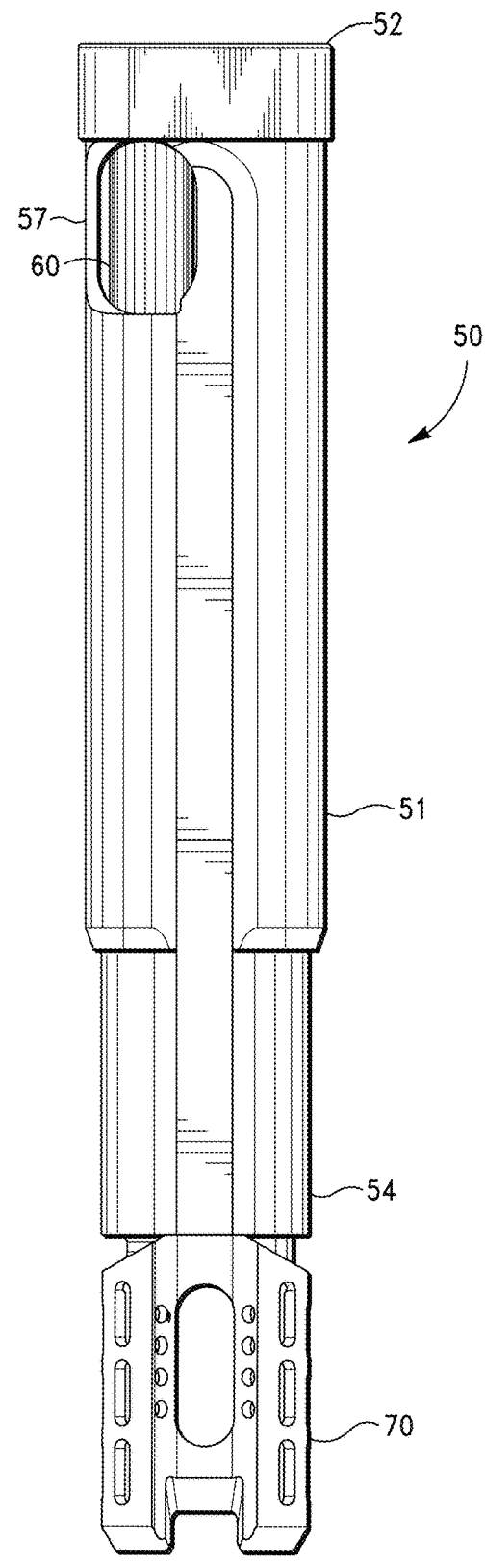
FIG. 5G is a perspective view of the prosthesis deployment assembly shown in FIG. 5A engaged to a prosthesis of the invention, in accordance with the invention.

Referring now to FIGS. 5A-5G, there is shown a preferred embodiment of a prosthesis deployment assembly of the invention (denoted "50" in FIG. 5G).

As illustrated in FIG. 5G, in a preferred embodiment, the prosthesis deployment assembly 50 comprises prosthesis engagement means configured and adapted to connect the prosthesis deployment assembly 50 to prostheses of the invention (prosthesis 70 shown in FIG. 5G) and guide the prostheses into pilot SI joint openings created by the defect creation assembly 30.

As illustrated in FIGS. 5A-5C, the prosthesis deployment assembly 50 comprises an elongated guide member 51 comprising proximal and distal ends 52, 54.

As further illustrated in FIGS. 5B and 5E, the elongated guide member 51 further comprises a prosthesis guide pin 56 that extends from the guide member distal end 54. As discussed in detail below and shown in FIG. 5G, the prosthesis guide pin 56 is sized and configured to seat in an internal prosthesis engagement member lumen 86a or 86b of the preferred prosthesis 70 of the invention.

As illustrated in FIGS. 5A, 5D and 5E, the elongated guide member 51 further comprises an internal lumen 58 that extends from the proximal end 52 of the elongated guide member 51 to the distal end 54 of the elongated guide member 51.

As illustrated in FIG. 5G, in a preferred embodiment of the invention, the internal lumen 58 is sized and configured to receive the prosthesis engagement rod 60 (i.e., prosthesis engagement means) of the prosthesis deployment assembly 50, discussed below.

Referring now to FIG. 5F, there is shown a preferred embodiment of a prosthesis engagement rod 60 of the invention. As illustrated in FIG. 5F, the prosthesis engagement rod 60 comprises a proximal end 62 and a threaded distal end 64, which, as discussed in detail below, is sized and configured to threadably engage an internal prosthesis engagement member lumen of a prosthesis of the invention, e.g., internal prosthesis engagement member lumens 86a and/or 86b of prosthesis 70.

As further illustrated in FIG. 5F, in a preferred embodiment, the proximal end 62 of the prosthesis engagement rod 60 comprises a knurled configuration to facilitate threading the prosthesis engagement rod 60 into an internal prosthesis engagement member lumen of a prosthesis of the invention.

Referring back to FIGS. 5A and 5B, to further facilitate threading the prosthesis engagement rod 60 into an internal prosthesis engagement member lumen of a prosthesis of the invention, in a preferred embodiment, the elongated guide member 51 further comprises an access port 57 that provides access to the knurled proximal end 62 of the prosthesis engagement rod 60 when positioned in the internal lumen 58 of the elongated guide member 51, as shown in FIG. 5G.

A further initial step in the minimally-invasive SI joint stabilization methods of the invention comprises providing a prosthesis configured and adapted to be inserted into, more preferably, press-fit into, i.e., interference engagement to, a pilot SI joint opening in a SI joint that is created by a defect creation assembly of the invention; particularly, defect creation assembly 30, and into and through articular cartilage and cortical bone 8 (and, in some instances, trabecular bone 10), which define the SI joint.

Various suitable prostheses that are configured and adapted to be inserted into a pilot SI joint opening created by a defect creation assembly of the invention are set forth in Co-pending priority application Ser. No. 13/857,977, which is expressly incorporated by reference herein.

According to the invention, the prostheses illustrated in FIGS. 12A-12C, 13A-13B, 14A-14C and 15A-15D of Co-pending priority application Ser. No. 13/857,977 are particularly suitable for insertion into pilot SI joint openings of the invention (i.e., SI joint openings 100, 200 described above) in a SI joint, and into and through articular cartilage and cortical bone 8 (and trabecular bone 10), which define the SI joint.

Referring now to FIGS. 6A-6I, there is shown a further prosthesis (denoted "70") of the invention, which is also particularly suitable for placement in pilot SI joint openings of the invention in a SI joint, and into and through articular cartilage and bone structures (i.e., cortical and trabecular bone 8, 10), which define the SI joint.

Figure 6A:
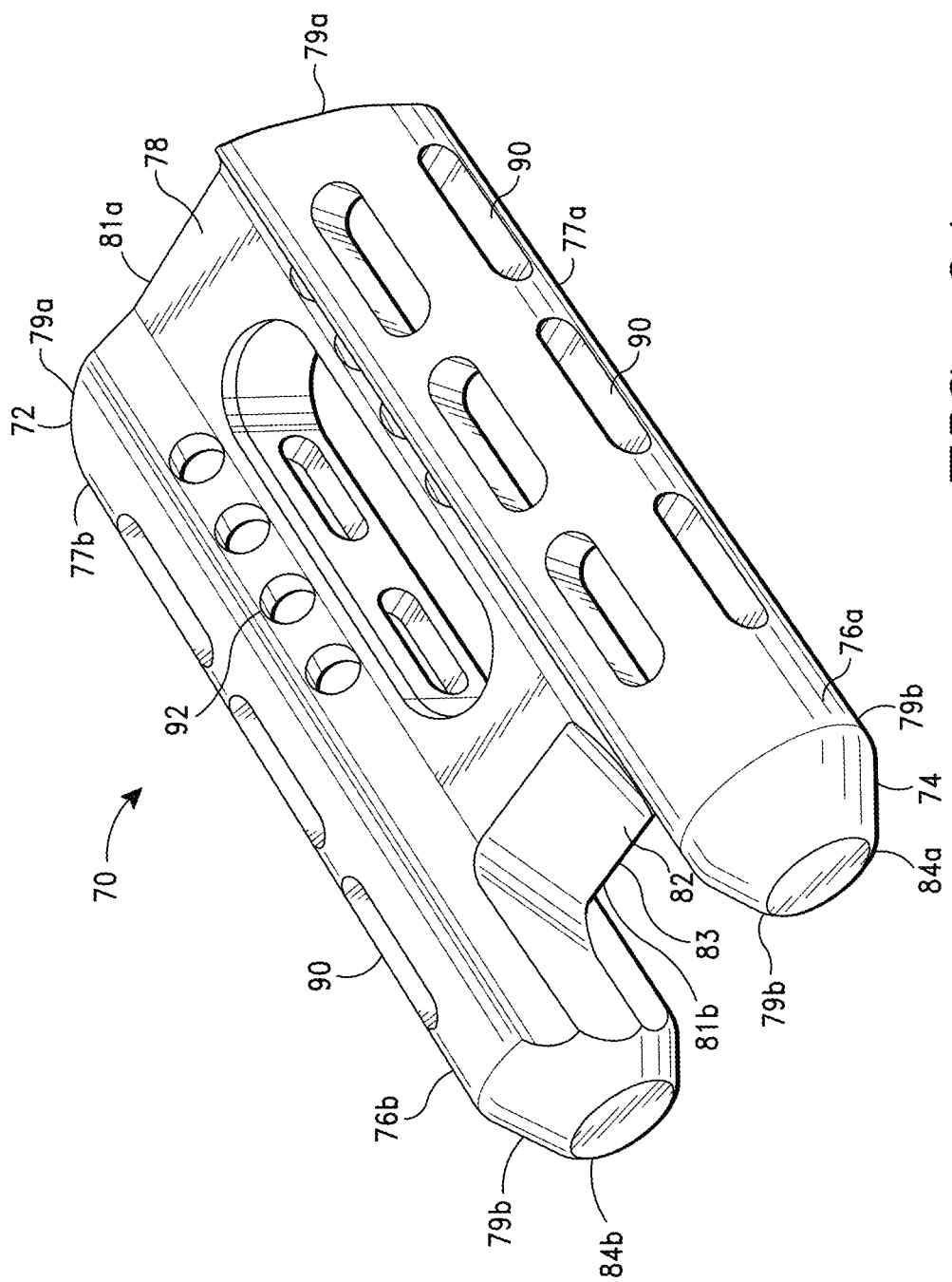
FIG. 6A is a perspective view of one embodiment of a prosthesis, in accordance with the invention.
Figure 6B:
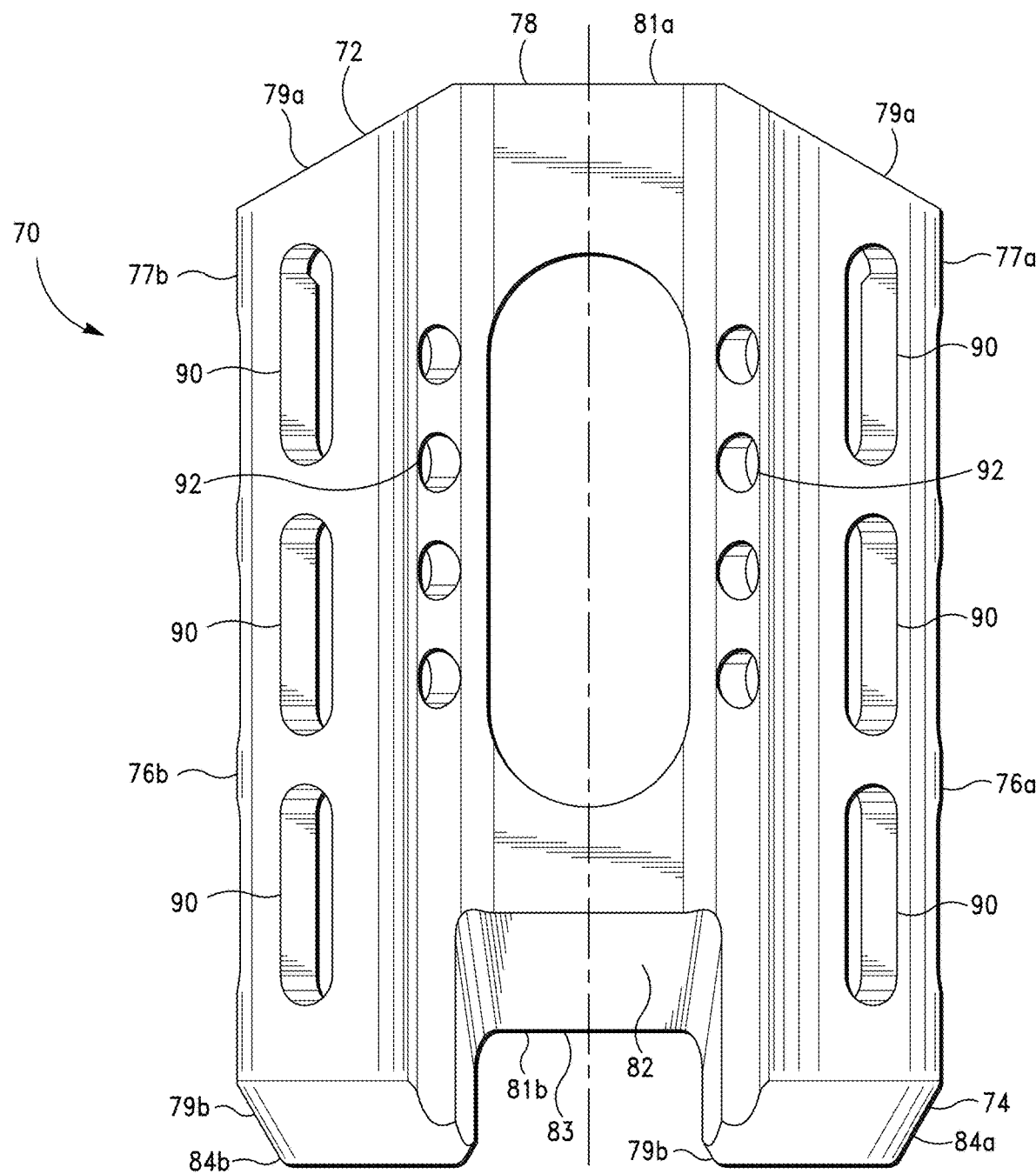
FIG. 6B is a top plan view of the prosthesis shown in FIG. 6A, in accordance with the invention.
Figure 6C:
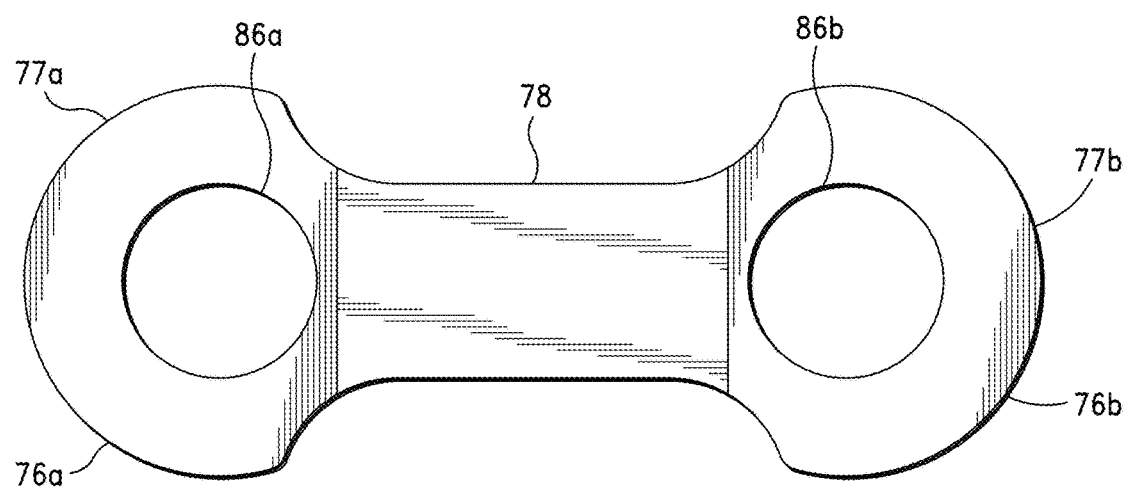
FIG. 6C is a rear plan view of the prosthesis shown in FIG. 6A, in accordance with the invention.
Figure 6D:
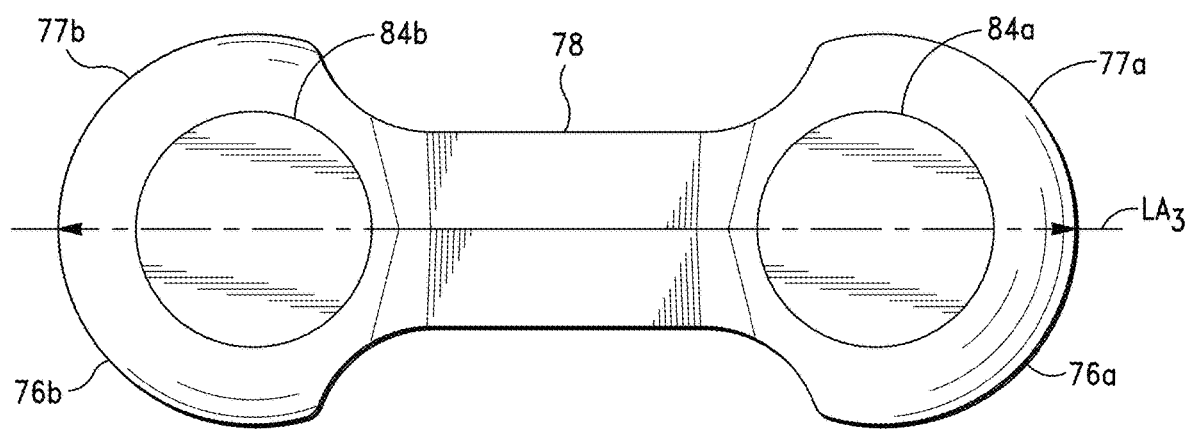
FIG. 6D is a front plan view of the prosthesis shown in FIG. 6A, in accordance with the invention.
Figure 6E:
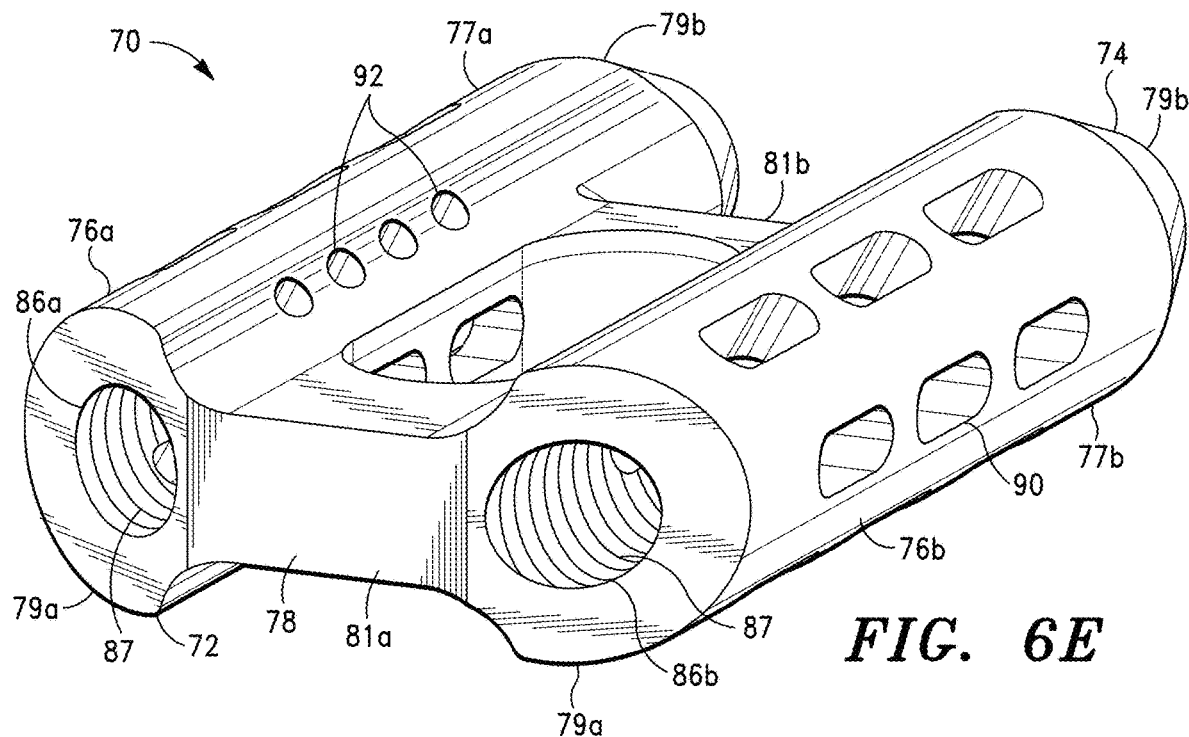
FIG. 6E is a rear perspective view of the prosthesis shown in FIG. 6A, in accordance with the invention.
Figure 6F:
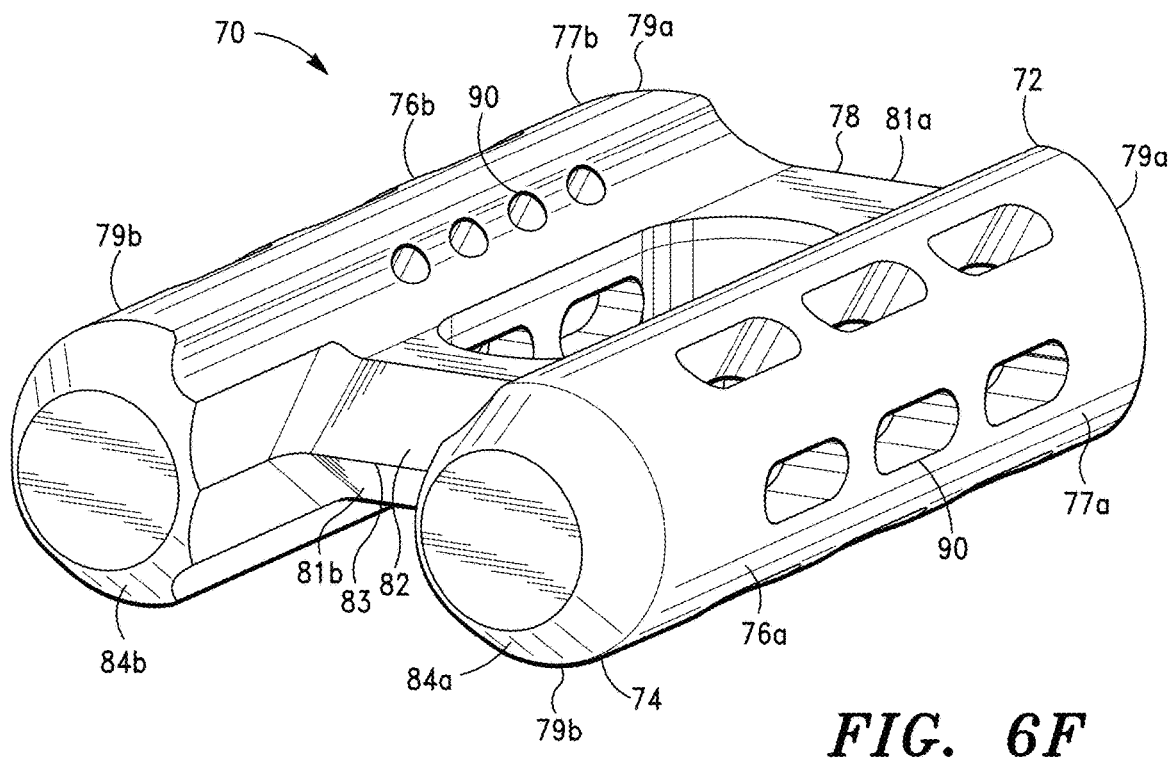
FIG. 6F is a front perspective view of the prosthesis shown in FIG. 6A, in accordance with the invention.

As illustrated in FIGS. 6A, 6E and 6F, the prosthesis 70 comprises a biocompatible and, hence, implantable member comprising proximal and distal ends 72, 74, and first and second elongated partially cylindrical sections 76a, 76b connected to a bridge section 78, whereby the prosthesis 70 comprises a continuous exterior surface comprising first and second partially cylindrical surface regions 77a, 77b.

As further illustrated in FIGS. 6A, 6E and 6F, the first and second partially cylindrical sections 76a, 76b comprise proximal and distal ends 79a, 79b. The bridge section 78 similarly comprises proximal and distal ends 81a, 81b.

According to the invention, the prosthesis 70 can comprise any suitable length from the proximal ends 79a to the distal ends 79b of the partially cylindrical sections 76a, 76b. In some embodiments, the prosthesis 70 comprises a length in the range of 20-50 mm, more preferably, a length in the range of 30-40 mm.

As illustrated in FIGS. 6C, 6E, 6F and FIGS. 4A and 4B, the first partially cylindrical surface region 77a preferably comprises a partially cylindrical surface region shape that corresponds to at least a portion of the first lobe region 103 of the pilot SI joint opening 100 and/or the sacrum guide portion 203 of the pilot SI joint opening 200, and/or the second lobe region 104 of the pilot SI joint opening 100 and/or the ilium guide portion 204 of the pilot SI joint opening 200, depending on the entry position of the prosthesis 70 into the pilot SI joint openings 100, 200.

The second partially cylindrical surface region 77b similarly preferably comprises a partially cylindrical surface region shape that corresponds to at least a portion of the first lobe region 103 of the pilot SI joint opening 100 and/or the sacrum guide portion 203 of the pilot SI joint opening 200, or the second lobe region 104 of the pilot SI joint opening 100 and/or the ilium guide portion 204 of the pilot SI joint opening 200, again depending on the entry position of the prosthesis 70 into the pilot SI joint openings 100, 200.

As illustrated in FIGS. 6A, 6B, 6F-6H, the distal end 81b of the bridge section 78 preferably comprises a taper region 82, which is configured and adapted to disrupt, i.e., cut into and through, articular cartilage and cortical bone 8 (and, in some aspects, trabecular bone 10), which define a SI joint.

According to the invention, the taper region 82 of the bridge section 78 can comprise various configurations including, without limitation, X-bevel, wedge-shaped or bevel, including top and bottom wedge bevels, Y-bevel, including top and bottom Y-bevels, and K-bevel configurations.

In some embodiments of the invention, the taper region 82 comprises two angled regions that intersect at a central point 83, i.e., pointed proximate the mid-region of the bridge section 78, such as shown in FIGS. 6A and 6F. In some embodiments, the taper region 82 comprises a single angled or sloped region defining a plane that intersects the plane defined by the bottom surface of the prosthesis 70, i.e., wedge shaped or bevel configuration.

Figure 8A:
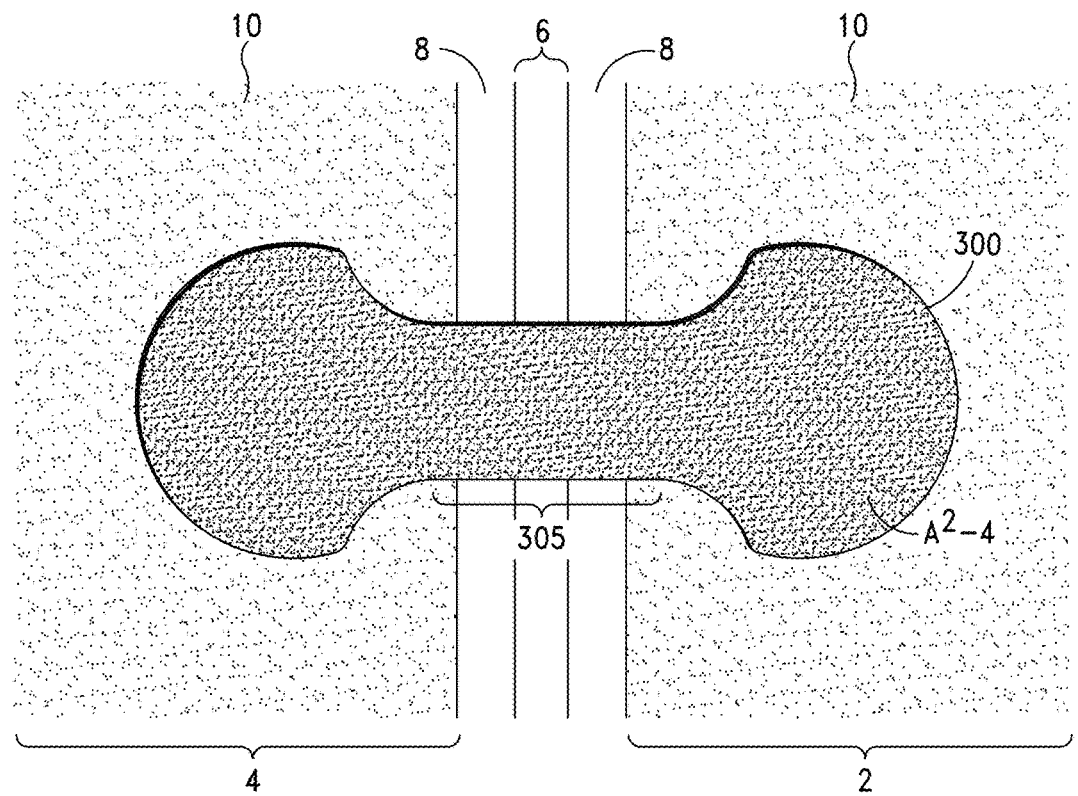
FIG. 8A is an illustration of the post-prosthesis insertion SI joint opening generated or induced when the prosthesis shown in FIG. 6A is inserted in the pilot SI joint opening shown in FIG. 4A, in accordance with the invention.
Figure 8B:
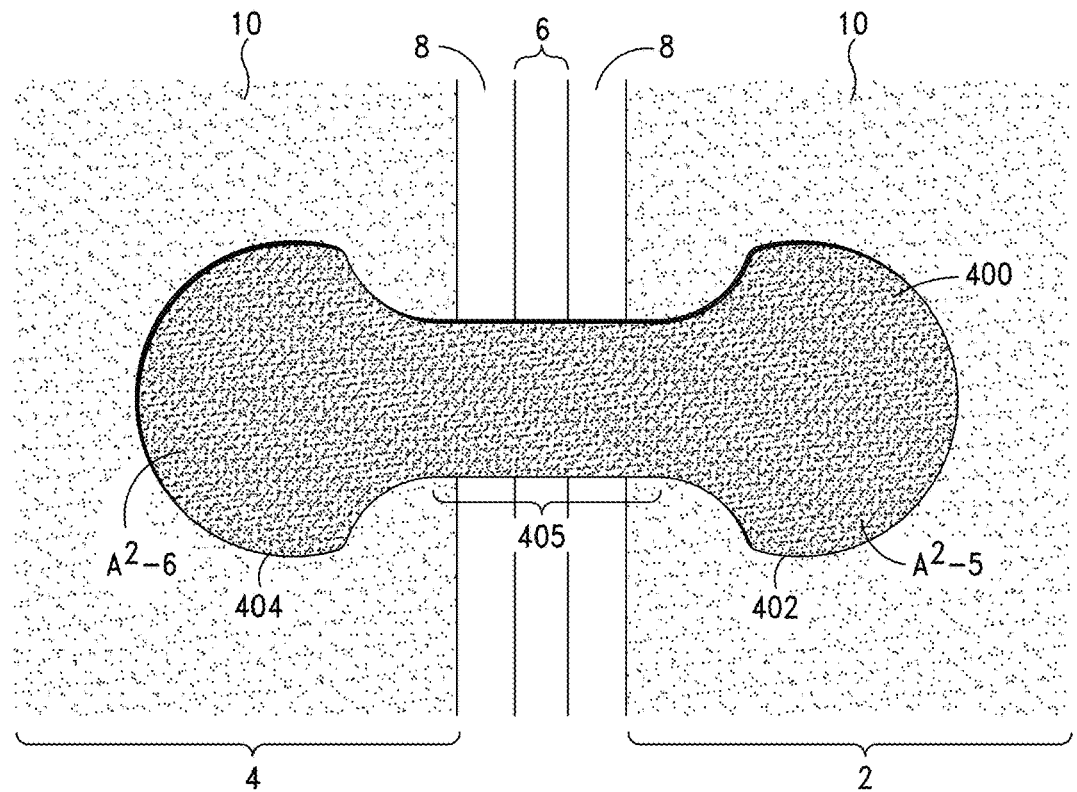
FIG. 8B is an illustration of the post-prosthesis insertion SI joint opening generated or induced when the prosthesis shown in FIG. 6A is inserted in the pilot SI joint opening shown in FIGS. 4B and/or 4C, in accordance with the invention.

In a preferred embodiment, the distal ends 79b of the first and second elongated partially cylindrical sections 76a, 76b also comprise tapered regions 84a, 84b, which facilitate (i) insertion of the distal ends 79b of the first and second elongated partially cylindrical sections 76a, 76b into the first and second lobe regions 103, 104 of the pilot SI joint opening 100 and/or the sacrum and ilium guide portions 203, 204 of the pilot SI joint opening 200, and (ii) as discussed in detail below, in some embodiments, transition of the pilot SI joint opening 100 from a first configuration and size (and, hence, cross-sectional area, i.e., $A^2_i$-1 shown in FIG. 4A) to a second expanded configuration and size (and, hence, cross-sectional area, i.e., $A^2$-4 shown in FIG. 8A) when the prosthesis 70 is inserted therein, and transition of the sacrum and ilium guide portions 203, 204 of pilot SI opening 200 from first configurations and sizes (and, hence, cross-sectional areas, i.e., $A^2_i$-2 and $A^2_i$-3 shown in FIG. 4B) to expanded second configurations and sizes (and, hence, cross-sectional areas, i.e., $A^2$-5 and $A^2$-6 shown in FIG. 8B) when the prosthesis 70 is inserted therein.

As illustrated in FIGS. 6C, 6E, and 6H, the first elongated partially cylindrical section 76a of the prosthesis 70 comprises an internal prosthesis engagement member lumen 86a that extends from the proximal end 79a of the first elongated partially cylindrical section 76a.

As illustrated in FIGS. 6C and 6E, the second elongated partially cylindrical section 76b of the prosthesis 70 also comprises an internal prosthesis engagement member lumen 86b that extends from the proximal end 79a of the first elongated partially cylindrical section 76b.

In a preferred embodiment, the internal prosthesis engagement member lumens 86a, 86b of the prosthesis 70 are sized and configured to receive the prosthesis guide pin 56 of the prosthesis deployment assembly 50 and, as indicated below, the prosthesis engagement rod 60 of the prosthesis deployment assembly 50.

As illustrated in FIGS. 6E and 6G, in a preferred embodiment, the internal prosthesis engagement member lumens 86a, 86b of the first and second elongated partially cylindrical sections 76a, 76b comprise a threaded region 87 proximate the proximal end 79a that is sized and configured to receive and threadably engage the threaded distal end 64 of the prosthesis engagement rod 60 of the prosthesis deployment assembly 50.

In a preferred embodiment, the internal prosthesis engagement lumens 86a, 86b are also configured to receive agents and compositions that further facilitate adhesion of the prosthesis 70 to the pilot SI openings 100, 200 of the invention and, thereby, sacrum and/or ilium, and the aforementioned biologically active agents and compositions, including osteogenic agents and compositions, and pharmacological agents and compositions that facilitate osseous or bone tissue ingrowth into the prosthesis 70 and healing of the SI joint bone structures.

Referring back to FIGS. 6A and 6B, in a preferred embodiment, the prosthesis 70 further comprises a plurality of slots 90 and holes 92, which preferably are in communication with the internal prosthesis engagement member lumens 86a, 86b.

In a preferred embodiment, the agents and compositions referenced above are adapted to extrude through the slots 90 and holes 92 of the prosthesis 70 when the prosthesis 70 is inserted in a pilot SI joint opening (i.e., pilot SI joint openings 100 or 200), to, as indicated above, (i) further facilitate adhesion of the prosthesis 70 to the pilot SI openings 100, 200 of the invention and, thereby, sacrum and/or ilium, and (ii) facilitate osseous or bone tissue ingrowth into the prosthesis 70 and healing of the SI joint bone structures.

Figure 6I:
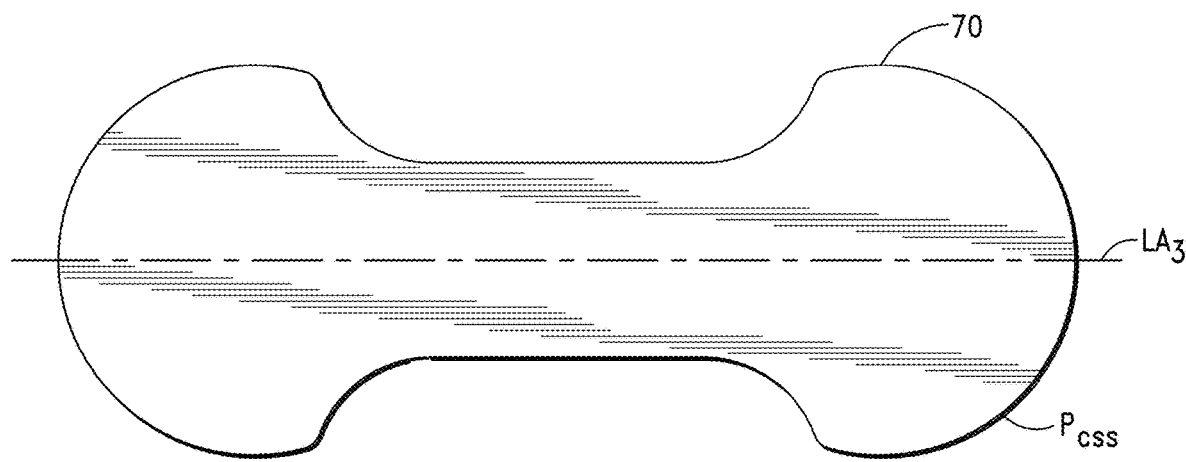
FIG. 6I is another rear plan view of the prosthesis shown in FIG. 6A showing the cross-sectional shape defined by the outer surface of the prosthesis, in accordance with the invention.

Referring now to FIG. 6I, according to the invention, the continuous exterior surface of the prosthesis 70, which is illustrated in FIGS. 6C and 6D, defines a prosthesis cross-sectional shape (denoted "$P_{CSS}$") having a longitudinal axis $LA_3$.

Figure 7A:
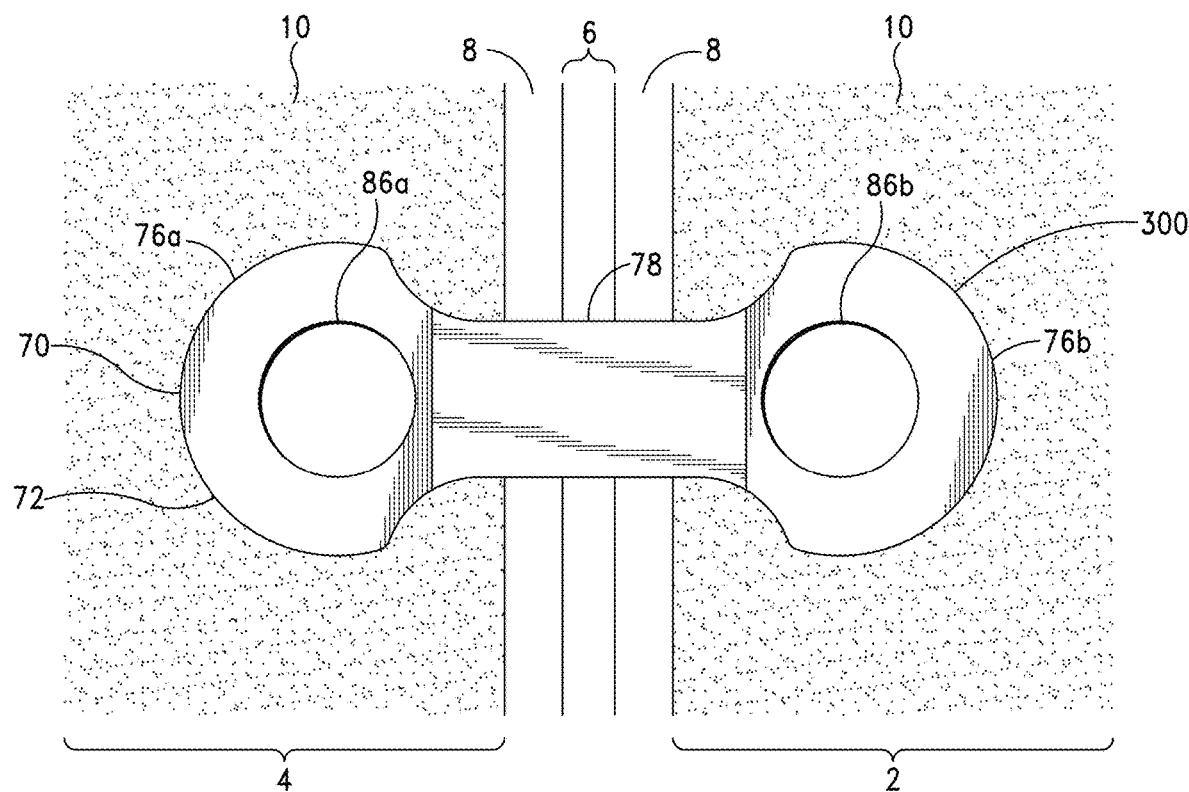
FIG. 7A is an illustration of the prosthesis shown in FIG. 6A inserted into the pilot SI joint opening shown in FIG. 4A and the resulting or induced post-prosthesis insertion SI joint opening, in accordance with the invention.

According to one embodiment of the invention, the length of the prosthesis cross-sectional shape $P_{CCS}$ along longitudinal axis $LA_3$ is greater than the length of the pilot SI joint opening 100, i.e., cross-sectional shape thereof illustrated in FIG. 4A, along the longitudinal axis $LA_2$ thereof, whereby, when the prosthesis 70 is inserted into pilot SI joint opening 100, as illustrated in FIG. 7A, the pilot SI opening 100 transitions to a post-prosthesis insertion SI joint opening 300 comprising a larger cross-sectional length shape that corresponds to the length of the prosthesis cross-sectional shape $P_{CCS}$.

As illustrated in FIG. 8A, in a preferred embodiment, when the prosthesis 70 is inserted into pilot SI joint opening 100, the cross-sectional area of the post-prosthesis insertion SI joint opening 300 also comprises a cross-sectional area (denoted "$A^2$-4") that is greater than the cross-sectional area $A^2_i$-1 of the pilot SI joint opening 100.

As further illustrated in FIG. 8A, the noncircular region 105 of pilot SI joint opening 100 also transitions to a much larger noncircular region (denoted "305"), which is achieved by virtue of the tapered bridge section 78 of the prosthesis 70 cutting into and through the articular cartilage and cortical bone 8, which define the SI joint 6, and the trabecular bone 10 proximate the SI joint 6.

Figure 7B:
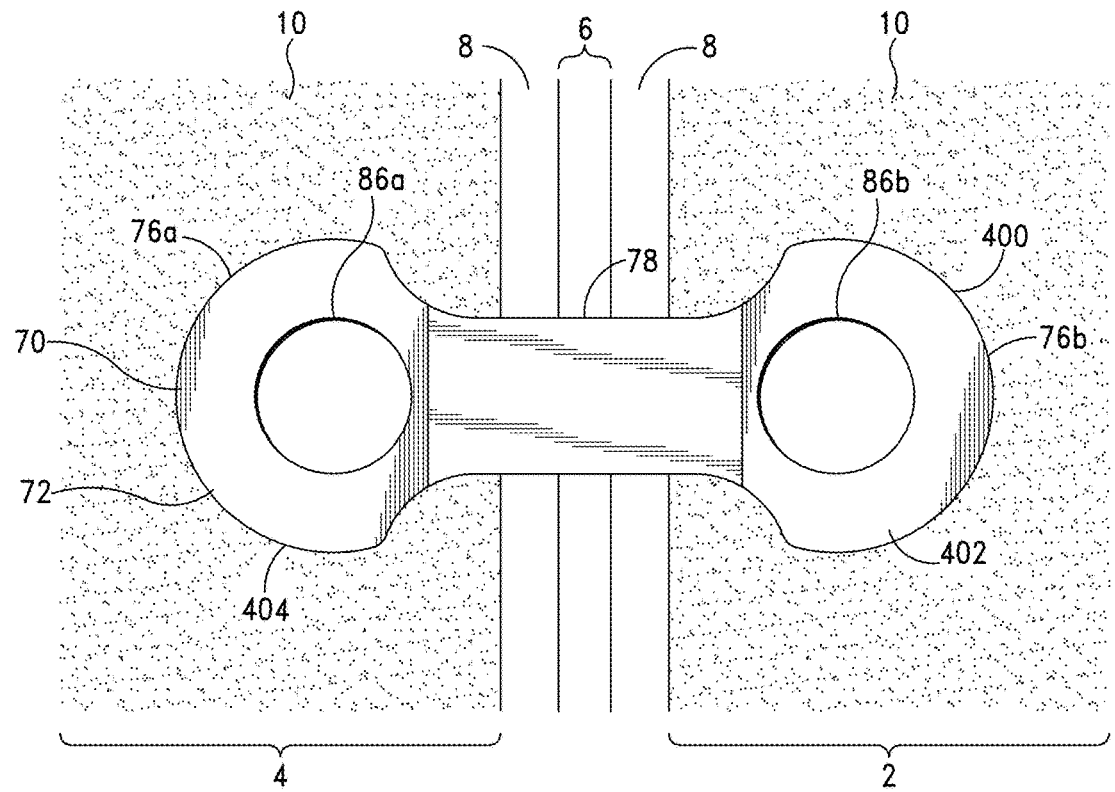
FIG. 7B is an illustration of the prosthesis shown in FIG. 6A inserted in the pilot SI joint opening shown in FIG. 4B and the resulting or induced post-prosthesis insertion SI joint opening, in accordance with the invention.

According to the embodiment of the invention, when the prosthesis 70 is inserted into pilot SI joint opening 200, as illustrated in FIG. 7B, the pilot SI joint opening 200 similarly transitions to a post-prosthesis insertion SI joint opening 400, wherein, as illustrated in FIG. 8B, the cross-sectional areas of the post-prosthesis sacrum and ilium guide portions of the post-prosthesis insertion SI joint opening 400 (now denoted "402" and "404", respectively) comprise greater cross-sectional areas (denoted "$A^2$-5" and "$A^2$-6").

As further illustrated in FIG. 8B, the post-prosthesis insertion SI joint opening 400 also comprises a noncircular region (denoted "405"), which is similarly achieved by virtue of the tapered bridge section 78 of the prosthesis 70 cutting into and through the articular cartilage and cortical bone 8, which define the SI joint 6, and the trabecular bone 10 proximate the SI joint 6.

As illustrated in FIGS. 6I, 8A and 8B, the post-prosthesis insertion SI joint openings 300, 400 also comprise cross-sectional shapes that correspond to the prosthesis cross-sectional shape "$P_{CSS}$" defined by the outer surface of the prosthesis 70, including the first and second elongated partially cylindrical sections 76a, 76b and bridge section 78.

In a preferred embodiment of the invention, to achieve sufficient expansion of the pilot SI joint openings 100, 200 when the prosthesis 70 is inserted therein, preferably, the cross-sectional areas of the regions defined by the first and second elongated partially cylindrical sections 76a, 76b of the prosthesis 70 are at least 0.05% greater than the cross-sectional areas defined by the first and second lobe regions 103, 104 of the pilot SI joint opening 100, and the cross-sectional areas defined by the sacrum and ilium guide portions 203, 204 of pilot SI joint opening 200.

In some embodiments of the invention, the cross-sectional areas of the regions defined by the first and second elongated partially cylindrical sections 76a, 76b of the prosthesis 70 are substantially equal to or slightly smaller, e.g., ≤0.05%, than the cross-sectional areas defined by the first and second lobe regions 103, 104 of the pilot SI joint opening 100, and the cross-sectional areas defined by the sacrum and ilium guide portions 203, 204 of pilot SI joint opening 200.

According to the invention, the prosthesis 70, as well as the prostheses disclosed in Co-pending priority application Ser. No. 13/857,977, can comprise various biocompatible materials, including metals and metal alloys, such as titanium, stainless-steel, cobalt-chromium alloys and nickel-titanium alloys.

The prosthesis 70, as well as the prostheses disclosed in Co-pending priority application Ser. No. 13/857,977, can also comprise various biocompatible polymers, including, without limitation, reinforced polymers, such as carbon fiber reinforced polymers and metal-framed polymers.

According to the invention, the prosthesis 70, as well as the prostheses disclosed in Co-pending priority application Ser. No. 13/857,977, can also comprise a porous structure to facilitate (i) adhesion of the prosthesis 70 to a post-prosthesis insertion SI joint opening of the invention; particularly, post-prosthesis insertion SI joint openings 300, 400 and, thereby, to SI joint bone structures, i.e., sacrum and ilium bone structures, and (ii) bone or osseous tissue ingrowth into the prosthesis 70.

According to the invention, the prosthesis 70, as well as the prostheses disclosed in Co-pending priority application Ser. No. 13/857,977, can comprise various exterior surface textures and roughness to facilitate or enhance engagement of the prosthesis to a post-prosthesis insertion SI joint opening, such as post-prosthesis insertion SI joint openings 300, 400, and, thereby, to SI joint bone structures, i.e., sacrum and ilium bone structures, and/or maintain engagement thereto and positioning therein. The surface of the prosthesis 70 (as well as the prostheses disclosed in Co-pending priority application Ser. No. 13/857,977) can, thus, comprise a roughness grade number of N1 (Ra=~0.025 μm), N2 (Ra=~0.05 μm), N3 (Ra=~0.1 μm), N4 (Ra=~0.2 μm), N5 (Ra=~0.4 μm), N6 (Ra=~0.08 μm), N7 (Ra=~1.6 μm), N8 (Ra=~3.2 μm), N9 (Ra=~6.3 μm), N10 (Ra=~12.5 μm), N11 (Ra=~25 μm) or N12 (Ra=~50 μm).

In some embodiments of the invention, the prosthesis 70, as well as the prostheses disclosed in Co-pending priority application Ser. No. 13/857,977, further comprise an outer coating.

In some embodiments, the outer coating comprises a biocompatible and, preferably, biodegradable adhesive composition. According to the invention, suitable adhesive compositions include, without limitation, poly(L-glutamic acid)-based compositions, poly(γ-glutamic acid)-based compositions, poly(alkyl cyano acrylate)-based compositions, polyacrylic acid-based compositions, including polyacrylic acid crosslinked with pentaerythritol and/or allyl sucrose, polyacrylic acid crosslinked with divinyl glycol and combinations thereof; fibrin-based compositions, collagen-based compositions, including collagen and poly(L-glutamic acid) compositions; albumin-based compositions, including BioGlue® (comprises purified bovine serum albumin (BSA) and glutaraldehyde); cyanoacrylate compositions, including butyl-2-cyanoacrylate adhesives (e.g., Indermil®, Histoacryl®, Histoacryl® Blue, and LiquiBand®) and octyl-2-cyanoacrylate adhesives (e.g., Dermabond®, SurgiSeal™, LiquiBand® Flex, and OctylSeal); poly(ethylene glycol) (PEG) based compositions, including FocalSeal®, Progel™, Duraseal™, DuraSeal™ Xact, Coseal® and ReSure Sealant; polysaccharide-based compositions, polypeptide-based compositions, and radiation curable materials, such as poly(glycerol-co-sebacate) acrylate (PGSA), discussed below.

In some embodiments, the outer coating comprises a biologically active agent composition comprising one of the aforementioned biologically active agents (referred to generally as fixation catalysts in Co-pending priority application Ser. No. 13/857,977) or pharmacological agent composition comprising one of the forementioned pharmacological agents.

In some embodiments, the outer coating comprises one of the aforementioned polymers and/or compositions comprising same.

In some embodiments, the aforementioned polymer compositions comprise one or more of the aforementioned biologically active agents or pharmacological agents.

In some embodiments of the invention, the polymer comprises poly(glycerol sebacate) (PGS) or a derivative thereof, including, without limitation, poly(glycerol-co-sebacate) acrylate (PGSA) and PGS co-polymers, such as poly(glycerol sebacate)-co-poly(ethylene glycol) (PGS-PEG); and/or composites thereof, e.g., PGS-hydroxyapatite (HA) composites and PGS-poly(ε-caprolactone) (PGS-PCL) composites, and compositions comprising same.

PGS and derivatives thereof possess a unique property of inducing remodeling of damaged osseous or bone tissue, such as at pilot SI joint openings, and, hence, healing of the associated bone structures when disposed proximate thereto.

As set forth in Loh, et al., *Poly(glycerol sebacate) Biomaterial: Synthesis and Biomedical Applications*, Journal of Materials Chemistry B, vol. 3(39), pp. 7641-7652 (2015) and indicated in Table 1 below, a further seminal property of PGS is that its physical state can be modulated during synthesis by controlling the "degree of esterification" via at least one crosslinking agent, e.g., methylene diphenyl diisocyanate (MDI).

TABLE 1

| Degree of Esterification | Physical State |
| --- | --- |
| ≤46% | Solid (Brittle Wax) |
| ~47%-64% | Semi-Solid (Soft Wax) |
| ~65%-75% | Viscous Liquid |
| ~76%-83% | Sticky Elastomer |
| ≥84% | Elastomer |

According to the invention, any suitable degree of esterification of PGS can be employed for PGS when employed in or for PGS based outer coatings (i.e., polymer compositions comprising PUS) and biologically active agent compositions of the invention.

In some embodiments, the PGS based outer coatings comprise a degree of esterification in the range of ~76%-83%, whereby the PGS exhibits adhesive properties, which will enhance engagement of prosthesis 70 (as well as the prostheses disclosed in Co-pending priority application Ser. No. 13/857,977) to the post-prosthesis insertion SI joint openings 300, 400 and, thereby, to the SI joint bone structures, i.e., sacrum and ilium bone structures.

As is well established, the physical state of poly(glycerol-co-sebacate) acrylate (PGSA) can also be modulated by combining the PGSA with a suitable photoinitiator and subjecting the PGSA to radiation.

Indeed, as set forth in Nijst, et al., "Synthesis and Characterization of Photocurable Elastomers from Poly(Glycerol-Co-Sebacate)," Biomacromolecules, vol. 8, no. 10, pp. 3067-3073 (2007), PGSA can be induced to transition from a liquid or flowable state to a solid elastomer state when combined with a photoinitiator, such as 2-hydroxy-1-[4-hydroxyethoxy) phenyl]-2-methyl-1-propanone (D 2959, Ciba Geigy), 2,2-dimethoxy-2-phenylacetophenone, titanocenes, fluorinated diaryltitanocenes, iron arene complexes, manganese decacarbonyl and methylcyclopentadienyl manganese tricarbonyl, and subjected to radiation, such as visible light; particularly, radiation in the range of approximately 380-750 run, and ultraviolet (UV) light, particularly, radiation in the range of 10-400 nm.

Thus, in some embodiments, a composition comprising PGSA (also referred to herein as a "PGSA based composition" and "fixation composition") is employed to enhance the engagement of the prosthesis 70 to a post-prosthesis insertion SI joint opening, such as post-prosthesis insertion SI joint openings 300, 400, and, thereby, SI joint bone structures, i.e., sacrum and ilium bone structures.

In such embodiments, the PGSA based composition (in a flowable state) is disposed in the internal prosthesis engagement member lumens 86a, 86b of the prosthesis 70, whereby the PGSA based composition is dispersed when the prosthesis 70 is positioned in the dysfunctional SI joint and fills any gaps between the prosthesis 70 and a post-prosthesis insertion SI joint opening of the invention; particularly, post-prosthesis insertion SI joint openings 300, 400, and thereafter cured via radiation and solidified, whereby the solidified PGSA enhances the engagement of the prosthesis 70 to the post-prosthesis insertion SI joint opening and, thereby, to the sacrum and ilium bone structures.

PGS and its derivatives; particularly, PGSA are also excellent platforms for delivery and, hence, administration of biologically active agents and pharmacological agents to mammalian tissue, including osseous or bone tissue.

Thus, in some embodiments of the invention, the PGS outer coatings and PGS and PGSA based compositions further comprise one or more of the aforementioned biologically active or pharmacological agents.

In accordance with one embodiment of the invention, after an incision is made to provide posterior access to the dysfunctional SI joint, the tool assembly described above is provided, and a desired prosthesis is provided, in this instance prosthesis 70 (also described above), the next steps in the method for stabilizing a dysfunctional SI joint comprise following:

the elongated guide probe 20 is advanced from a posterior approach into the incision site and positioned in the dysfunctional SI joint;

after the elongated guide probe 20 is advanced into the incision site and positioned in the dysfunctional SI joint, the elongated guide probe 20 is inserted into the distal end 36 of the defect creation assembly 30 and into and through the guide member lumen 38 of the defect creation assembly 30;

after the elongated guide probe 20 is inserted into the distal end 36 of the defect creation assembly 30 and into and through the guide member lumen 38 of the defect creation assembly 30, the defect creation assembly 30 is then advanced (i.e., slidably translated along the elongated guide probe 20) from a posterior approach along the elongated guide probe 20 into the dysfunctional SI joint to a desired prosthesis implant position;

after the defect creation assembly 30 is advanced along the elongated guide probe 20 into the dysfunctional SI joint to a desired prosthesis implant position, a pilot SI joint opening is then created with the defect creation assembly 30;

after the pilot SI joint opening is created, the defect creation assembly 30 and elongated guide probe 20 are retracted from the dysfunctional SI joint;

after the defect creation assembly 30 and elongated guide probe 20 are retracted from the dysfunctional SI joint, the prosthesis deployment assembly 50 is connected to the prosthesis (in this instance prosthesis 70), wherein the prosthesis guide pin 56 of the prosthesis deployment assembly 50 is inserted into the first internal prosthesis engagement member lumen 86a of the first elongated partially cylindrical section 76a of the prosthesis, i.e., prosthesis 70, and the threaded distal end 64 of the prosthesis engagement rod is threaded into the second internal prosthesis engagement member lumen 86b of the second elongated partially cylindrical section 76b of the prosthesis, i.e., prosthesis 70, or, alternatively, the prosthesis guide pin 56 of the prosthesis deployment assembly 50 is inserted into the second internal prosthesis engagement member lumen 86b of the first elongated partially cylindrical section 76b of the prosthesis, i.e., prosthesis 70, and the threaded distal end 64 of the prosthesis engagement rod is threaded into the first internal prosthesis engagement member lumen 86a of the first elongated partially cylindrical section 76a of the prosthesis, i.e., prosthesis 70;

after the prosthesis deployment assembly 50 is connected to the prosthesis, i.e., prosthesis 70, the prosthesis, i.e., prosthesis 70, is advanced into the pilot SI joint opening with the prosthesis deployment assembly 50, wherein the prosthesis, i.e., prosthesis 70, is press-fit into the pilot SI joint opening and induces a transition of the pilot SI joint opening to a larger post-prosthesis insertion SI joint opening; and after the prosthesis is advanced into the pilot SI joint opening with said prosthesis deployment assembly 50, the prosthesis deployment assembly 50 is retracted out of the dysfunctional SI joint.

In some embodiments of the invention, wherein the pilot SI joint created by the defect creation assembly 30 comprises pilot SI joint opening 100 or 200 described above, when the prosthesis, i.e., prosthesis 70, is press-fit into the pilot SI joint opening, the first sacrum opening cross-sectional shape transitions to a second sacrum cross-sectional shape comprising a third area, and the first ilium opening cross-sectional shape transitions to a second ilium opening cross-sectional shape comprising a fourth area, the third area of the second sacrum cross-sectional shape being larger than the first area of the first sacrum cross-sectional shape, and the fourth area of the second ilium cross-sectional shape being larger than the second area of the first ilium cross-sectional shape.

In some embodiments, the method for stabilizing a dysfunctional SI joint further comprises the step of placing one of the aforementioned biologically active or pharmacological compositions in one or both of the internal prosthesis engagement member lumens 86a, 86b of the prosthesis, i.e., prosthesis 70, after the prosthesis deployment assembly 50 is retracted out of the dysfunctional SI joint, whereby the biologically active or pharmacological composition is dispersed through the slots 90 and holes 92 of the prosthesis 70 and administered to the osseous tissue of the SI joint bone structures, i.e., sacrum and ilium bone structures, when the prosthesis 70 is positioned therein.

In some embodiments, the method for stabilizing a dysfunctional SI joint further comprises the step of collecting the dislodged bone material, e.g., cortical bone, trabecular bone and bone marrow, after the pilot SI joint opening is created for subsequent use in a biologically active composition of the invention.

In some embodiments of the invention, the method for stabilizing a dysfunctional SI joint further comprises the steps of (i) providing an image capture apparatus configured and adapted to capture images of at least the elongated guide probe 20 and defect creation assembly 30 when disposed in the body, and, particularly, disposed proximate and in the dysfunctional SI joint, and (ii) capturing images and, hence, positions and orientations of the elongated guide probe 20 and defect creation assembly 30 when disposed in the body, and, particularly, during advancement of the elongated guide probe 20 and defect creation assembly 30 toward and into the dysfunctional SI joint.

According to the invention, suitable image capture apparatus comprise a fluoroscope, a CT system, ultrasound system, radiography system, and magnetic resonance imaging system.

In some embodiments of the invention, the method for stabilizing a dysfunctional SI joint further comprises the steps of (i) providing a drill guide assembly that guides the elongated guide probe 20 and defect creation assembly 30 to desired positions proximate to and in the dysfunctional SI joint to properly place the pilot SI joint opening and, thereby, prosthesis 70 in the dysfunctional SI joint, and (ii) after the incision is made to provide posterior access to the dysfunctional SI joint, positioning the drill guide assembly proximate the dysfunctional SI joint to guide the elongated guide probe 20 and defect creation assembly 30 to desired positions proximate to and in the dysfunctional SI joint.

Figure 9A:
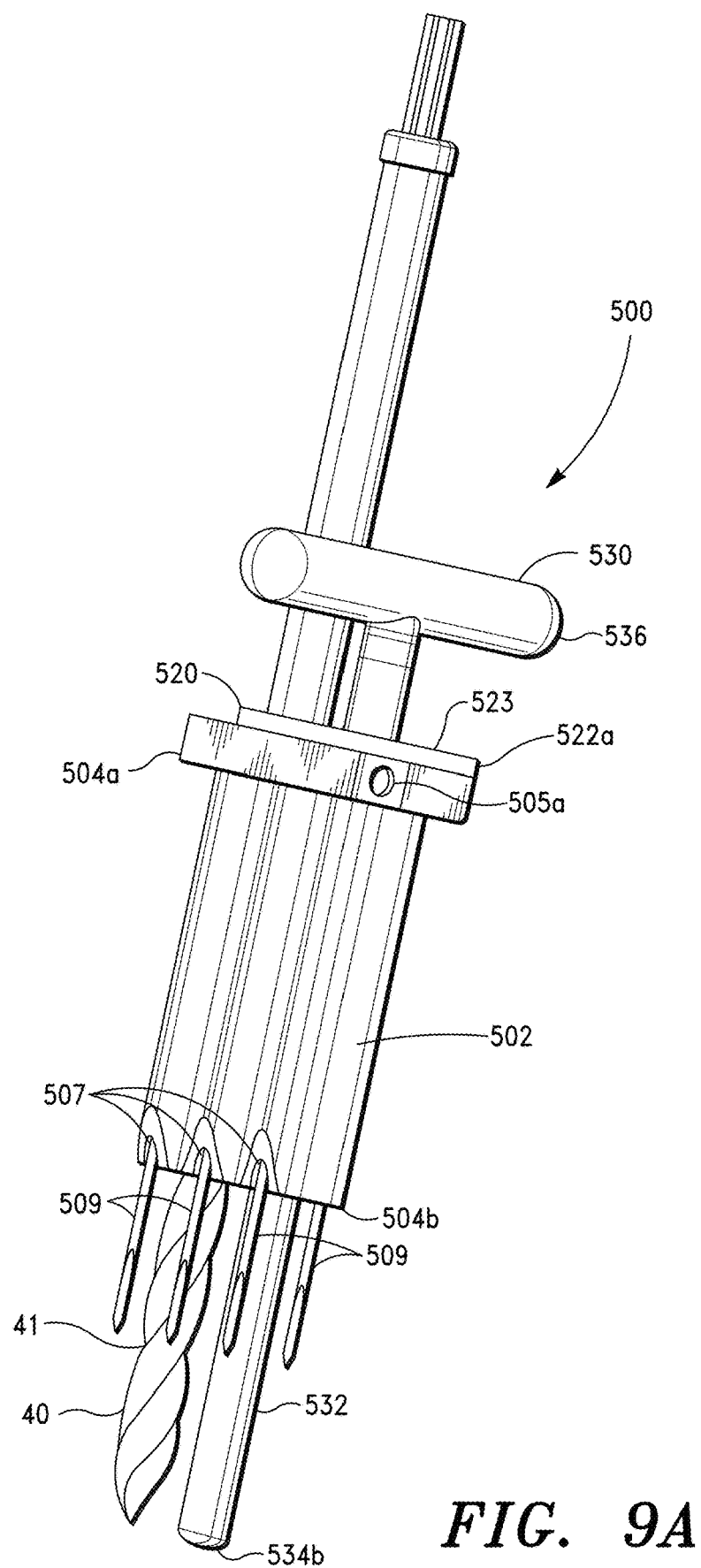
FIG. 9A is a perspective view of one embodiment of drill guide assembly, in accordance with the invention.

Referring now to FIG. 9A, there is shown a preferred embodiment of a drill guide assembly 500 of the invention.

As illustrated in FIG. 9A, the drill guide assembly 500 comprises an access sleeve 502, drill guide 520 and a guide pin 530.

Figure 9B:
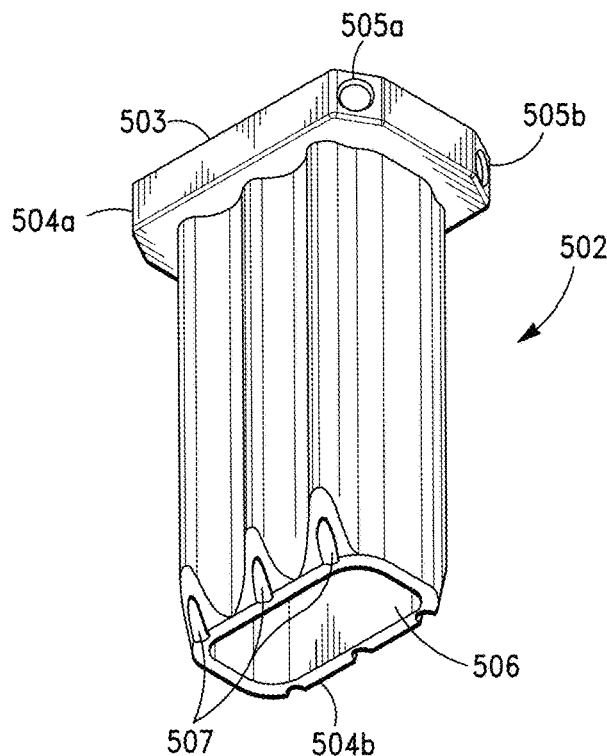
FIG. 9B is a perspective view of the access sleeve of the drill guide assembly shown in FIG. 9A, in accordance with the invention.
Figure 9C:
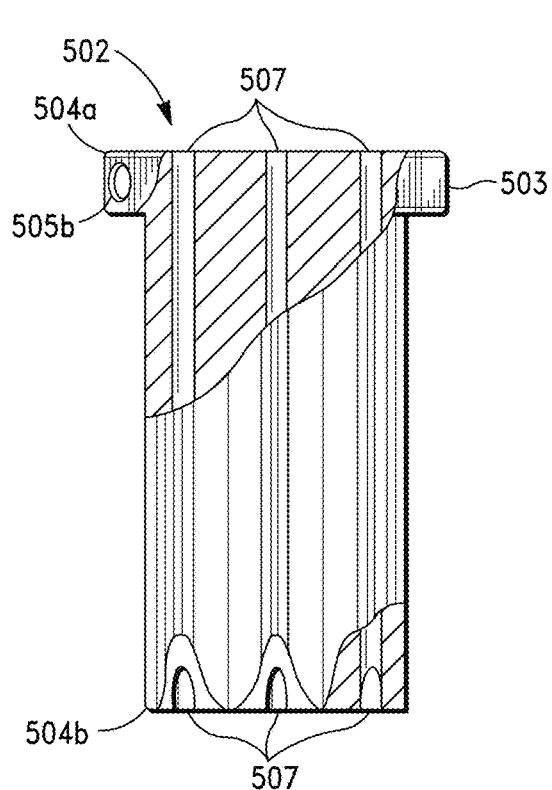
FIG. 9C is a front plan view of the access sleeve shown in FIG. 9B, in accordance with the invention.
Figure 9D:
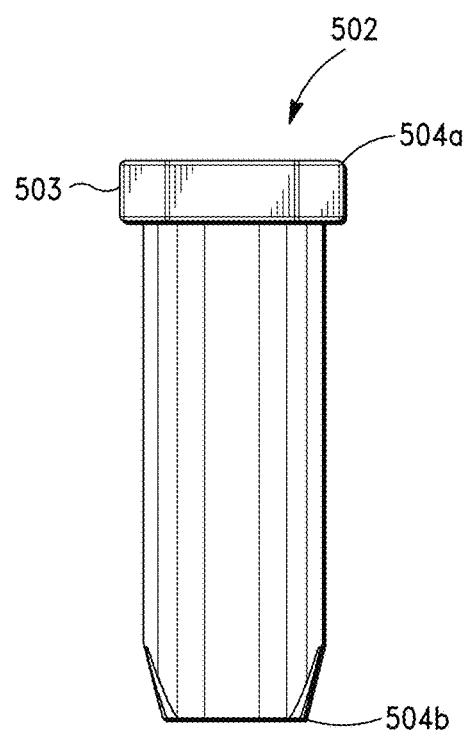
FIG. 9D is a right-side plan view of the access sleeve shown in FIG. 9B, in accordance with the invention.

Referring now to FIGS. 9B-9D, there is shown a preferred embodiment of the access sleeve 502.

As illustrated in FIGS. 9B-9D, the access sleeve 502 comprises proximal and distal ends 504a, 504b, an internal opening 506 that extends from the proximal end 504a to the distal end 504b of the access sleeve 502, and a plurality of lumens 507, which, as illustrated in FIG. 9A, are sized and configured to receive and position Kirschner wires (K-wires) 509 or similar pin structures therein.

As illustrated in FIG. 9A, in a preferred embodiment, the access sleeve internal opening 506 is sized and configured to receive and position the drill guide 520 therein.

As further illustrated in FIGS. 9B and 9D, the proximal end 504a of the access sleeve 502 comprises a planar region 503, which, as illustrated in FIG. 9A, is configured to seat the proximal end 522a of the drill guide 520 (discussed below) thereon.

In a preferred embodiment, as additionally shown in FIGS. 9B and 9D, the proximal end 504a of the access sleeve 502, i.e., planar region 503, further comprises two (2) threaded holes 505a, 505b, which are preferably disposed on opposing edge regions of the planar region 503. According to the invention, the threaded holes 505a, 505b are sized and configured to receive the threaded end 514 of the access sleeve handle 510, discussed below.

Figure 9F:
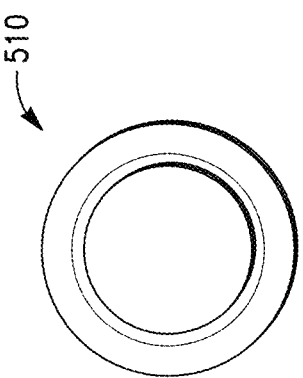
FIG. 9F is an end plan view of the access sleeve handle shown in FIG. 9E, in accordance with the invention.
Figure 9E:
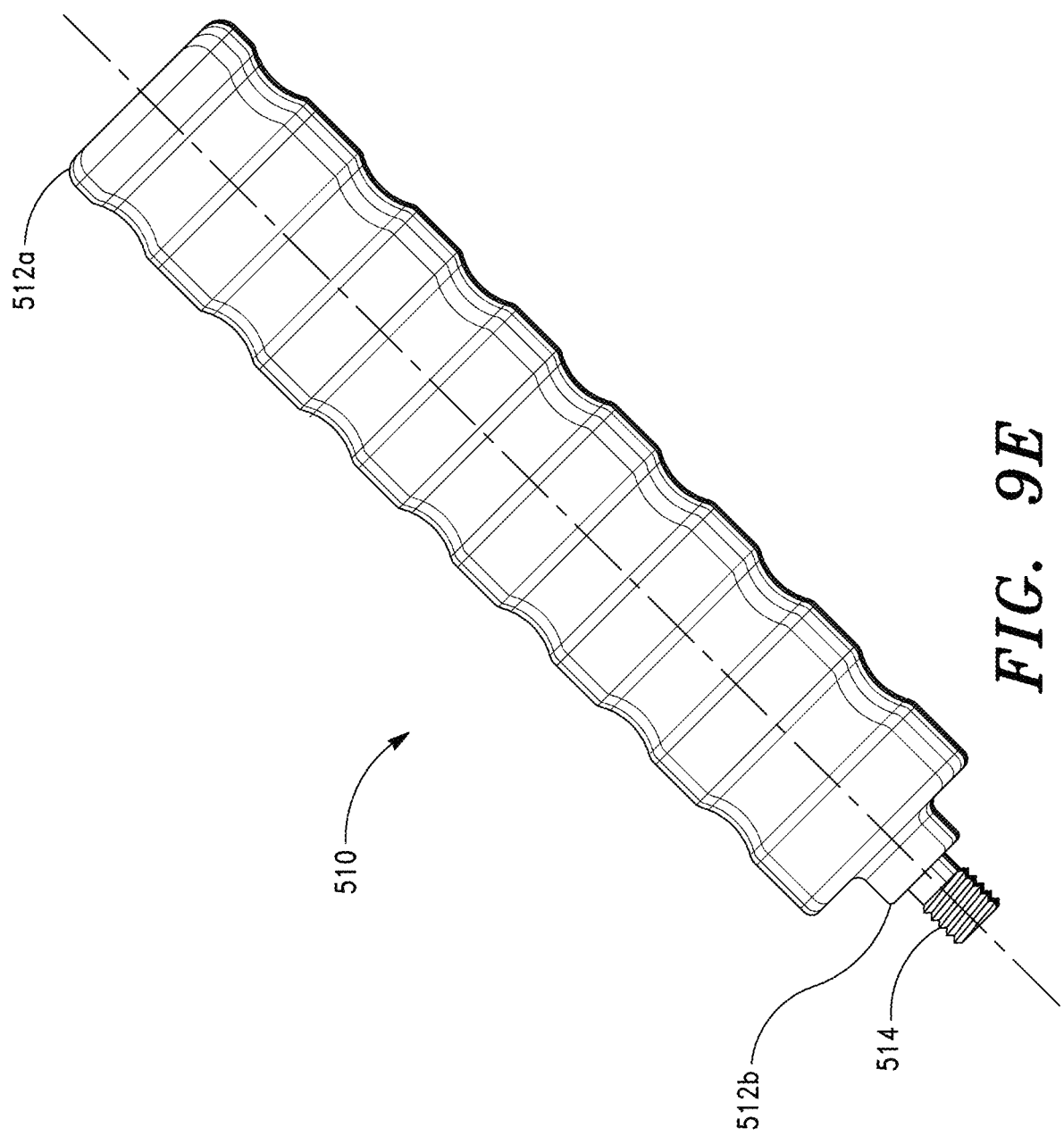
FIG. 9E is a perspective view of one embodiment of an access sleeve handle that is configured to engage the access sleeve shown in FIG. 9B, in accordance with the invention.
Figure 9I:
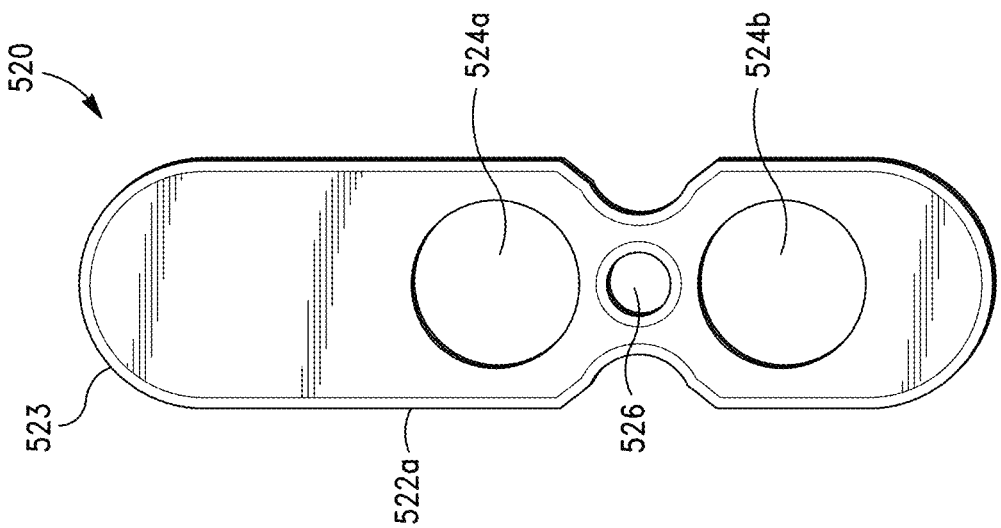
FIG. 9I is a top plan view of the drill guide shown in FIG. 9G, in accordance with the invention.
Figure 9J:
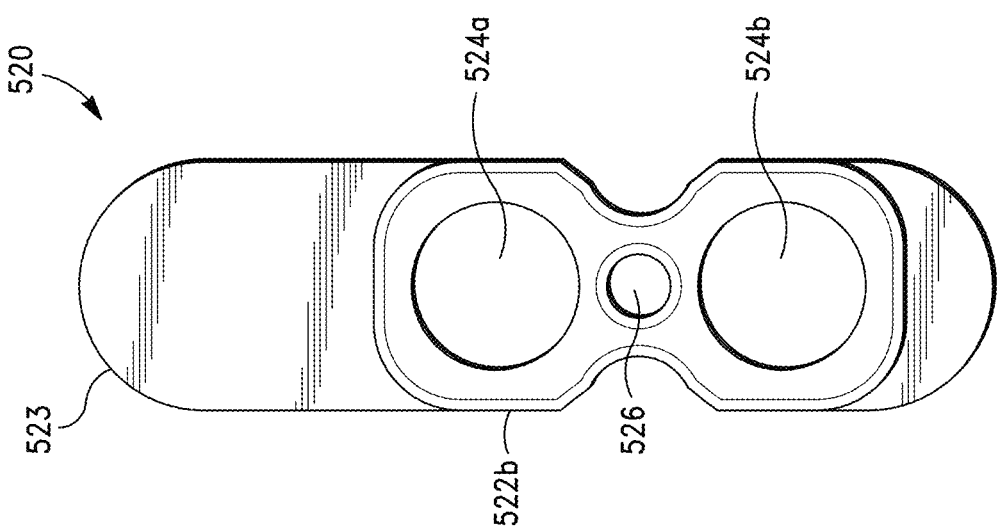
FIG. 9J is a bottom plan view of the drill guide shown in FIG. 9G, in accordance with the invention.

Referring now to FIGS. 9E and 9F, there is shown a preferred embodiment of the access sleeve handle 510.

As illustrated in FIGS. 9E and 9F, the access sleeve handle 510 preferably comprises an elongated cylindrical shaped member comprising proximal and distal ends 512a, 512b.

As further illustrated in FIG. 9E, in a preferred embodiment, the distal end 512b of the access sleeve handle 510 comprises a threaded extension 514 that is sized and configured to cooperate with the threaded holes 505a, 505b of the access sleeve 502, whereby the access sleeve handle 510 can be threadably engaged to the access sleeve 502.

Referring now to FIGS. 9G-9J, there is shown a preferred embodiment of the drill guide 520.

As illustrated in FIGS. 9E-9J, the drill guide 520 comprises proximal and distal ends 522a, 522b, a pair of drill guide lumens 524a, 524b and a drill guide medial lumen 526; the drill guide lumens 524a, 524b and drill guide medial lumen 526 extending from the proximal end 522a to the distal end 522b of the drill guide 520.

Figure 9L:
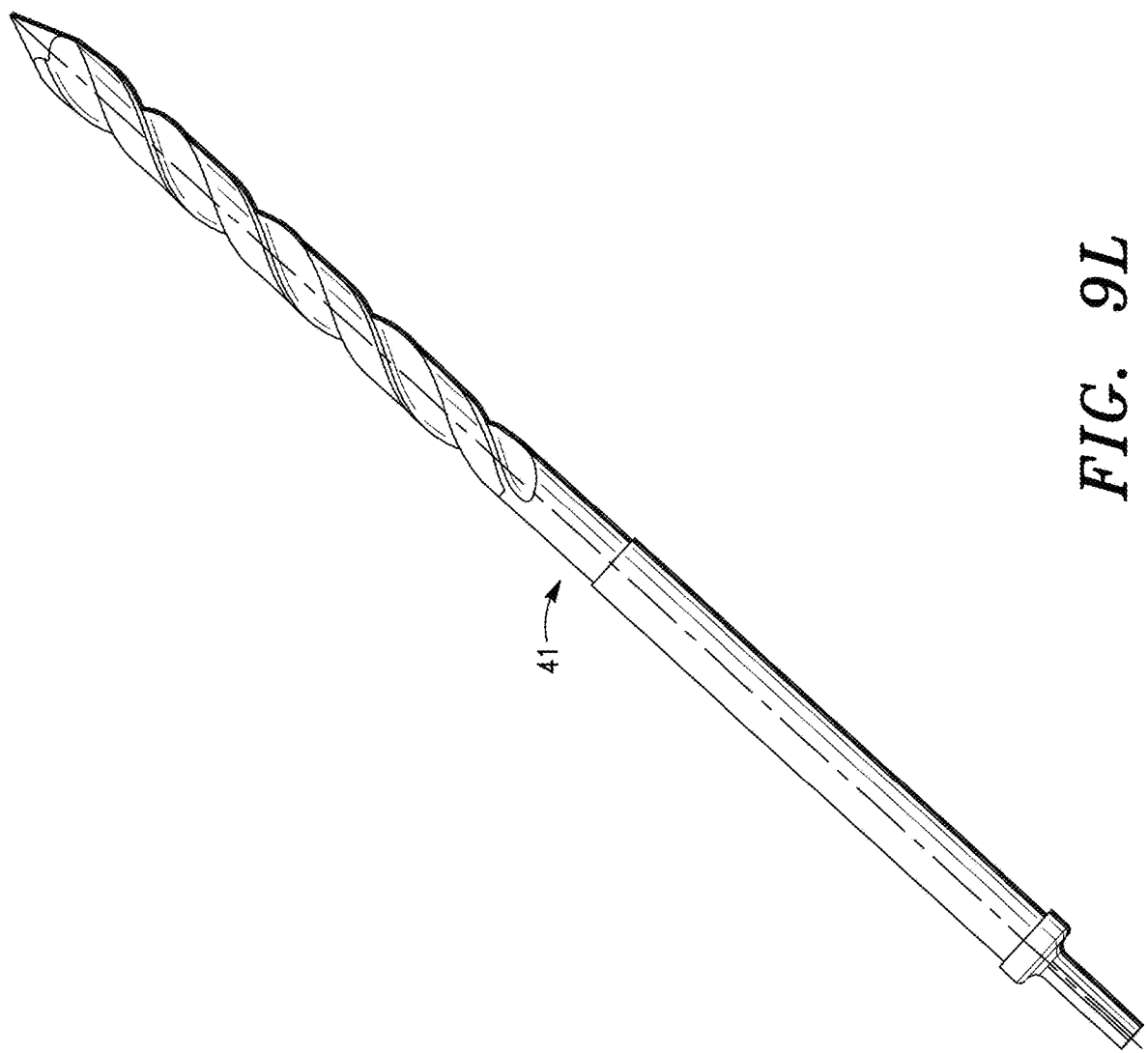
FIG. 9L is a perspective view of the bone dislodging apparatus, i.e., drill bit, shown in FIG. 9A, in accordance with the invention.

As illustrated in FIG. 9A, in a preferred embodiment, the drill guide lumens 524a, 524b are sized and configured to receive (i) a bone dislodging system 40 of the defect creation assembly 30, in this instance, the drill bit 41 shown in FIG. 9L, and (ii) the guide pin 530 shown in FIG. 9K and discussed below.

In a preferred embodiment, the drill guide medial lumen 526 is sized and configured to receive and guide the elongated guide probe 20 of the invention to a desired position proximate the dysfunctional SI joint.

According to the invention, the drill guide internal lumens 524a, 524b and drill guide medial lumen 526 can also be sized and configured to receive various other suitable instruments, such as surgical scopes, center punches, location pins, drill probes and drill stop assemblies, to facilitate the creation of a pilot SI joint opening.

Referring back to FIGS. 9G and 9H, in a preferred embodiment, the proximal end 522a of the drill guide 520 comprises a planar configuration comprising an extended region 523, which, as illustrated in FIG. 9A, is sized and configured to abut the proximal end 504a of the access sleeve 502 to position the drill guide 520 therein.

Figure 9K:
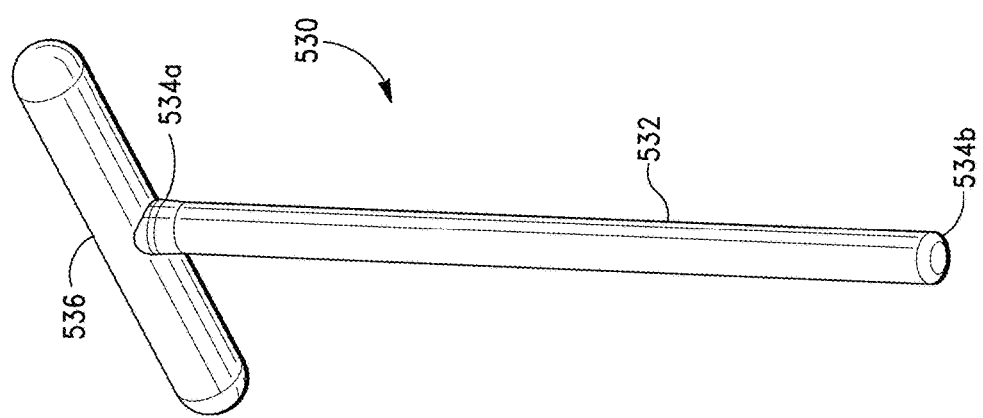
FIG. 9K is a perspective view of the guide pin of the drill guide assembly shown in FIG. 9A, in accordance with the invention.

Referring now to FIG. 9K, there is shown one embodiment of a guide pin 530 of the invention.

As illustrated in FIG. 9K, the guide pin 530 preferably comprises an elongated guide member 532 comprising proximal and distal ends 534a, 534b. The guide pin 530 further comprises a handle 536 that is operatively connected to the proximal end 534a of the guide member 532.

According to the invention, in the noted embodiments, after an incision is made to provide posterior access to the dysfunctional SI joint, the tool assembly described above is provided, a desired prosthesis is provided, in this instance prosthesis 70 (also described above), and the drill guide assembly 500 described above is provided, the next steps in the method for stabilizing a dysfunctional SI joint comprise the following:

the drill guide assembly 500 is assembled, i.e., the drill guide 520 is positioned in the access sleeve 502;

after the drill guide assembly 500 is assembled, the drill guide assembly 500 is advanced through the incision site and positioned proximate the dysfunctional SI joint;

after the drill guide assembly 500 is advanced through the incision site and positioned proximate the dysfunctional SI joint, K-wires 509 are inserted into and through lumens 507 of the access sleeve 502 of the drill guide assembly 500 and into dysfunctional SI joint structures, e.g., SI joint soft and hard tissue, to position and stabilize the drill guide assembly 500 proximate the dysfunctional SI joint;

after the K-wires 509 are inserted into and through the lumens 507 of the access sleeve 502 of the drill guide assembly 500 and into the dysfunctional SI joint structures, the elongated guide probe 20 is placed in and through the drill guide medial lumen 526 of the drill guide 520 and advanced from a posterior approach into the dysfunctional SI joint;

after the elongated guide probe 20 is advanced into the dysfunctional SI joint, the elongated guide probe 20 is inserted into the defect creation assembly 30 of the invention;

after the elongated guide probe 20 is inserted into the tool assembly, the defect creation assembly 30, i.e., bone dislodging system 40 thereof, is then advanced though a first drill guide internal lumen, i.e., drill guide internal lumen 524a, of the drill guide 520 and into the dysfunctional SI joint;

after the bone dislodging system 40 of the defect creation assembly 30 is advanced into the dysfunctional SI joint, a first portion of a pilot SI joint opening is then created in the dysfunctional SI joint with the bone dislodging system 40 of the defect creation assembly 30;

after the first portion of the pilot SI joint opening is created in the dysfunctional SI joint, the bone dislodging system 40 of the defect creation assembly 30 is retracted out of the dysfunctional SI joint and drill guide internal lumen 524a of the drill guide 520;

after the bone dislodging system 40 of the defect creation assembly 30 is retracted out of the dysfunctional SI joint and drill guide internal lumen 524a of the drill guide 520, the guide pin 530 of the drill guide assembly 500 is inserted into the first portion of the pilot SI joint opening to further stabilize the drill guide assembly 500 proximate the dysfunctional SI joint;

after the guide pin 530 of the drill guide assembly 500 is inserted into the first portion of the pilot SI joint opening, the bone dislodging system 40 of the defect creation assembly 30 is advanced though the second drill guide internal lumen, i.e., drill guide internal lumen 524b, of the drill guide 520 and into the dysfunctional SI joint;

after the bone dislodging system 40 of the defect creation assembly 30 is advanced into the dysfunctional SI joint, a second portion of the pilot SI joint opening is then created in the dysfunctional SI joint with the bone dislodging system 40 of the defect creation assembly 30;

after the second portion of the pilot SI joint opening is created in the dysfunctional SI joint, the bone dislodging system 40 of the defect creation assembly 30 is retracted out of the dysfunctional SI joint and drill guide internal lumen 524b of the drill guide 520, and the elongated guide probe 20 is removed from the defect creation assembly 30;

after the bone dislodging system 40 of the defect creation assembly 30 is retracted out of the dysfunctional SI joint and drill guide internal lumen 524b of the drill guide 520, and the elongated guide probe 20 is removed from the defect creation assembly 30, the guide pin 530 is retracted out of the first portion of the pilot SI joint opening;

after the bone dislodging system 40 of the defect creation assembly 30 is retracted out of the dysfunctional SI joint and drill guide internal lumen 524b of the drill guide 520, and the elongated guide probe 20 is removed from the defect creation assembly 30, the drill guide 520 is removed from the access sleeve 502 of the drill guide assembly 500;

after the drill guide 520 is removed from the access sleeve 502 of the drill guide assembly 500, the elongated guide probe 20 is retracted out of the dysfunctional SI joint;

after the elongated guide probe 20 is retracted out of the dysfunctional SI joint, the prosthesis deployment assembly 50 is connected to the prosthesis (in this instance prosthesis 70), wherein, as indicated above. the prosthesis guide pin 56 of the prosthesis deployment assembly 50 is inserted into the first internal prosthesis engagement member lumen 86a of the first elongated partially cylindrical section 76a of the prosthesis, i.e., prosthesis 70, and the threaded distal end 64 of the prosthesis engagement rod is threaded into the second internal prosthesis engagement member lumen 86b of the second elongated partially cylindrical section 76b of the prosthesis, i.e., prosthesis 70, or, alternatively, the prosthesis guide pin 56 of the prosthesis deployment assembly 50 is inserted into the second internal prosthesis engagement member lumen 86b of the first elongated partially cylindrical section 76b of the prosthesis, i.e., prosthesis 70, and the threaded distal end 64 of the prosthesis engagement rod is threaded into the first internal prosthesis engagement member lumen 86a of the first elongated partially cylindrical section 76a of the prosthesis, i.e., prosthesis 70;

after the prosthesis deployment assembly 50 is connected to the prosthesis, i.e., prosthesis 70, the prosthesis, i.e., prosthesis 70, is inserted into and through the internal opening 506 of the access sleeve 502 and advanced into the pilot SI joint opening with the prosthesis deployment assembly 50, wherein the prosthesis, i.e., prosthesis 70, is press-fit in the pilot SI joint opening and induces a transition of the pilot SI joint opening to a larger post-prosthesis insertion SI joint opening;

after the prosthesis is advanced into the pilot SI joint opening with said prosthesis deployment assembly 50, the prosthesis deployment assembly 50 is retracted out of the dysfunctional SI joint;

after the prosthesis deployment assembly 50 is retracted out of the dysfunctional SI joint, the K-wires 509 are retracted out of the dysfunctional SI joint structures and the lumens 507 of the access sleeve 502 of the drill guide assembly 500; and after the K-wires 509 are retracted out of the dysfunctional SI joint structures and the lumens 507 of the access sleeve 502 of the drill guide assembly 500, the access sleeve 502 is retracted out of the subject's body.

In some embodiments of the invention, when the prosthesis, i.e., prosthesis 70, is press-fit into the pilot SI joint opening, the cross-sectional shape of the first portion of the pilot SI joint opening transitions to a second cross-sectional shape comprising a larger cross-sectional area, and the cross-sectional shape of the second portion of the pilot SI joint opening similarly transitions to a second cross-sectional shape comprising a larger cross-sectional area.

In some embodiments, the noted method for stabilizing a dysfunctional SI joint similarly further comprises the step of placing one of the aforementioned biologically active or pharmacological compositions in one or both of the internal prosthesis engagement member lumens 86a, 86b of the prosthesis, i.e., prosthesis 70, after the prosthesis deployment assembly 50 is retracted out of the dysfunctional SI joint, whereby the biologically active or pharmacological composition is dispersed through the slots 90 and holes 92 of the prosthesis 70 and administered to the osseous tissue of the SI joint bone structures, i.e., sacrum and ilium bone structures, when the prosthesis 70 is positioned therein.

In some embodiments of the invention, the noted method similarly further comprises the steps of (i) providing one of the aforementioned image capture apparatus and (ii) capturing images and, hence, positions and orientations of the elongated guide probe 20 and defect creation assembly 30 when disposed in the body, and, particularly, during advancement of the elongated guide probe 20 and defect creation assembly 30 toward and into the dysfunctional SI joint.

EXAMPLES

The following example is provided to enable those skilled in the art to more clearly understand and practice the present invention. The example should not be considered as limiting the scope of the invention, but merely as being illustrated as representative thereof.

An adult male, age 42 presented with a traumatic injury proximate the SI joint, resulting in a dysfunctional SI joint and significant pain associated therewith, i.e., a visual analog pain score (VAS) of approximately 8.0.

A CT scan was initially performed to determine the full extent of the patient's injury, check for any SI joint abnormalities and plan the stabilization procedure, including the prosthesis structure required to stabilize the dysfunctional SI joint.

The stabilization procedure was performed in accord with the method that includes the drill guide assembly summarized above. The specifics of the procedure were as follows:

Prosthesis

The prosthesis selected and, hence, provided for the procedure was similar to prosthesis 70 illustrated in FIGS. 6A-6H and described in detail above. The prosthesis comprised a length of 30 mm and the elongated partially cylindrical sections, i.e., barrels, of the prosthesis comprised a diameter of 7.5 mm. The prosthesis was sourced from Applicant, i.e., Tenon Medical, Inc., and referred to as a CATAMARAN SIJ Fixation System™.

The prosthesis included an autograft bone material, which was placed in the barrels of the prosthesis after the prosthesis was implanted in the dysfunctional SI joint.

Posterior Inferior Surgical Approach

The initial incision was placed along the lateral lip of the posterior third of the iliac crest to the posterior superior spine, which provided a prosthesis entry point into the dysfunctional SI joint through the posterior ligaments at approximately the S3 level. The trajectory of the prosthesis was toward the mid-point of the S1 end plate and the sacral promontory.

Creation of Pilot SI Joint Opening

The pilot SI joint opening was created with the defect creation assembly shown in FIGS. 3B and 3C, and described above. The bone dislodging apparatus of the assembly comprised a drill assembly and associated drill bit.

The pilot SI joint opening, which was similar to pilot SI joint opening 200 described above, was created by drilling a first opening in the sacrum bone structure and a second opening in the ilium bone structure (such as shown in FIG. 4B) with the drill assembly.

Radiological Assessment

Figure 10A:
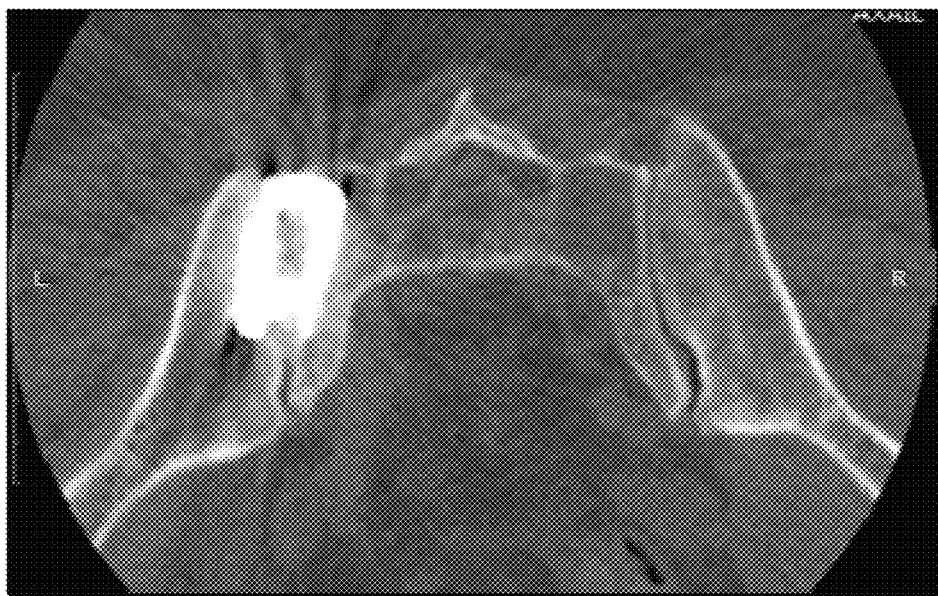
FIGS. 10A and 10B are CT scan images of a patient's SI joint at six (6) months following an SI joint stabilization procedure with the prosthesis shown in FIG. 6A, in accordance with the invention.
Figure 10B:
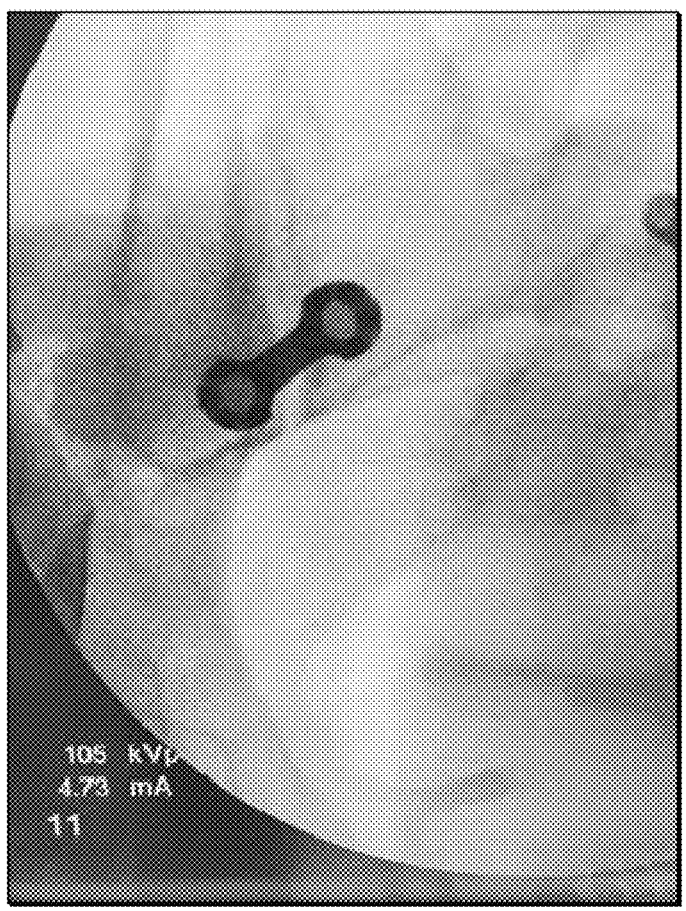

CT scan images of the patient's SI joint six (6) months after the SI joint stabilization procedure, which are shown in FIGS. 10A and 10B, reflect (i) secure and proper placement of the prosthesis in the SI joint, (ii) substantial solid bridging of osseous tissue, and, hence, bone across the SI joint and, (iii) substantial ossification around the prosthesis.

Post-Procedure SI Joint Pain Relief and Function

Figure 11:
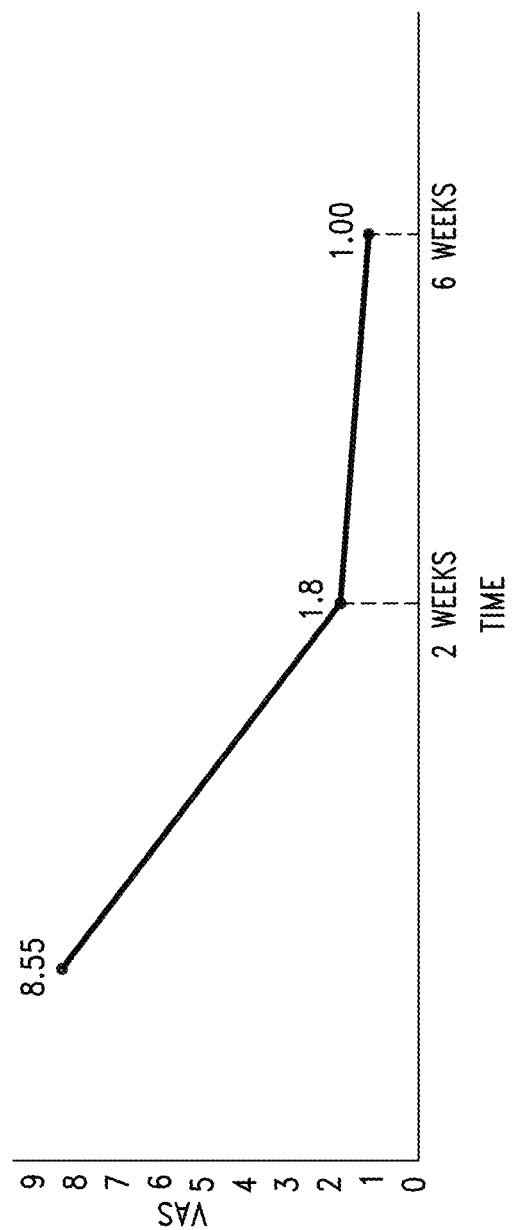
FIG. 11 is a graphical illustration of a patient's visual analog pain score over a six (6) week period of time following an SI joint stabilization procedure with the prosthesis shown in FIG. 6A, in accordance with the invention.

After a recovery period of fourteen (14) days, the patient reported that the pain had been substantially reduced. Indeed, as shown in FIG. 11, fourteen (14) days after the procedure a visual analog pain score (VAS) of 1.8 was achieved.

The patient was also subjected to a series of post procedure tests to determine the stability of the SI joint and mobility of the musculoskeletal structures of the pelvic and lumbar regions proximate the SI joint. The results were very favorable. The patient tested positive to the flexion abduction and external rotation (FABER) test. The patient also responded very favorably to Gaenslen, thigh thrust, compression and distraction tests.

The tests thus confirmed that the post procedure SI joint was stabilized and that the musculoskeletal structures of the pelvic and lumbar regions proximate thereto were restored to a near normal level.

As will readily be appreciated by one having ordinary skill in the art, the present invention provides numerous advantages compared to prior art methods for stabilizing dysfunctional SI joints. Among the advantages are the following:

the provision of improved minimally-invasive SI joint stabilization methods and associated systems and apparatus, which facilitate posterior trajectory placement of prostheses in dysfunctional SI joints and, thereby, stabilization of the dysfunctional SI joints;

the provision of improved minimally-invasive SI joint stabilization methods that disrupt less tissue and muscles, and avoid nerves and large blood vessels;

the provision of improved minimally-invasive SI joint stabilization methods and associated systems and apparatus, which effectively ameliorate pain associated with SI joint dysfunction;

the provision of improved SI joint prostheses, which can readily be employed in minimally-invasive SI joint stabilization methods and possess optimal structural properties to effectively stabilize dysfunctional SI joints; and the provision of improved SI joint prostheses that can readily be employed in minimally-invasive SI joint stabilization methods, which facilitate remodeling of damaged osseous tissue and regeneration of new osseous tissue and osseous tissue structures.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A method for stabilizing a dysfunctional sacroiliac (SI) joint of a subject, said dysfunctional SI joint disposed between and defined by a sacrum bone structure and an ilium bone structure, comprising the steps of:
   a. providing an elongated guide probe, a defect creation assembly, a prosthesis and a prosthesis deployment assembly,
   said elongated guide probe adapted to be advanced into said dysfunctional SI joint,
   said defect creation assembly adapted to access said dysfunctional SI joint in a posterior trajectory,
   said defect creation assembly further adapted to create a pilot SI joint opening in said dysfunctional SI joint, said pilot SI joint opening comprising a sacrum structure opening and an ilium structure opening,
   said defect creation assembly comprising a defect creation assembly proximal end, a defect creation assembly distal end disposed opposite said defect creation assembly proximal end, and a guide member lumen that extends through said defect creation assembly, said guide member lumen adapted to receive said guide probe therein,
   said prosthesis sized and adapted to be advanced into said pilot SI joint opening in said posterior trajectory, said prosthesis comprising a hollow monolithic member, said monolithic member comprising a first elongated section, a second elongated section, and a bridge section, said bridge section disposed between said first elongated section and said second elongated section in any direction,
   said monolithic member further comprising a first longitudinal axis,
   said first elongated section configured to be advanced into said sacrum bone structure when said prosthesis is said advanced into said dysfunctional SI joint in said posterior trajectory,
   said second elongated section configured to be advanced into said ilium bone structure when said prosthesis is said advanced into said dysfunctional SI joint in said posterior trajectory,
   said bridge section configured to be advanced into said intraarticular region of said dysfunctional SI joint when said prosthesis is said advanced into said dysfunctional SI joint in said posterior trajectory,
   said first elongated section comprising a first open proximal end, a first closed distal end and a first length from said first open proximal end to said first closed distal end,
   said first elongated section further comprising a first internal elongate lumen extending from said first open proximal end to said first closed distal end, said first internal elongate lumen comprising a second longitudinal axis and first internal threads extending from said first open proximal end of said first elongated section,
   said first elongated section further comprising a first plurality of slots, said first plurality of slots in communication with said first elongate lumen of said first elongated section,
   said first elongated section further comprising a first tapered region disposed on said first closed distal end,
   said second elongated section comprising a second open proximal end, a second closed distal end and a second length from said second open proximal end to said second closed distal end,
   said second elongated section further comprising a second internal elongate lumen extending from said second open proximal end to said second closed distal end, said second internal elongate lumen comprising a third longitudinal axis and second internal threads extending from said second open proximal end of said second elongated section,
   said second elongated section further comprising a second plurality of slots, said second plurality of slots in communication with said second elongate lumen of said second elongated section,
   said second elongated section further comprising a second tapered region disposed on said second closed distal end,
   said bridge section comprising a fourth longitudinal axis, a closed proximal end, a third closed distal end, and a third length from said closed proximal end to said third closed distal end, said third length of said bridge section being less than said first length of said first elongated section and said second length of said second elongated section,
   said bridge section further comprising an elongate opening disposed between said closed proximal end and said third closed distal end of said bridge section and extending through said bridge section, said elongate opening being in communication with said first plurality of slots and, thereby said first elongate lumen of said first elongated section and said second plurality of slots and, thereby said second elongate lumen of said second elongated section,
   said bridge section further comprising a third tapered region disposed on said third distal end, said third tapered region comprising a gradually decreasing thickness along said fourth longitudinal axis of said bridge section, said fourth longitudinal axis of said bridge section being coincident with said first longitudinal axis of said monolithic member,
   said third tapered region comprising a first tapered section and an opposing second tapered section, said first tapered section and said second tapered section intersecting at said third closed distal end of said bridge section,
   said prosthesis deployment assembly configured and adapted to engage said prosthesis and advance said prosthesis into said pilot SI joint opening in said posterior trajectory,
   said prosthesis deployment assembly comprising an elongated guide member and a prosthesis engagement rod, said elongated guide member comprising a guide member proximal end and a guide member distal end,
   said prosthesis deployment assembly further comprising a guide member lumen that extends through said elongated guide member from said guide member proximal end to said guide member distal end, said guide member lumen sized and configured to receive said prosthesis engagement rod therein,
   said prosthesis engagement rod comprising an engagement rod proximal end and an engagement rod distal end, said engagement rod distal end comprising first external threads, said prosthesis engagement rod sized and configured to be first advanced into said first internal elongate lumen of said prosthesis and second advanced into said second internal elongate lumen of said prosthesis, said first external threads of said prosthesis engagement rod sized and configured to cooperate with said first internal threads of said first internal elongate lumen of said prosthesis when said prosthesis engagement rod is said first advanced into said first internal elongate lumen, and cooperate with said second internal threads of said second internal elongate lumen of said prosthesis when said prosthesis engagement rod is said second advanced into said second elongate lumen of said prosthesis, said elongated guide member further comprising a prosthesis guide pin that extends from said guide member distal end, said prosthesis guide pin sized and configured to be third advanced into said first internal elongate lumen of said prosthesis and fourth advanced into said second internal elongate lumen of said prosthesis;

b. making an incision in and through tissue of said subject to provide posterior access to said subject's dysfunctional SI joint;

c. advancing said elongated guide probe in and through said incision and into said dysfunctional SI joint;

d. inserting said elongated guide probe into and through said guide probe lumen of said defect creation assembly;

e. advancing said defect creation assembly along said elongated guide probe into said dysfunctional SI joint in said posterior trajectory;

f. creating said pilot SI joint opening in said dysfunctional SI joint with said defect creation assembly;

g. retracting said defect creation assembly and said elongated guide probe from said dysfunctional SI joint;

h. engaging said prosthesis deployment assembly to said prosthesis, wherein said prosthesis engagement rod is said first advanced into said first internal elongate lumen of said prosthesis and said cooperates with said first internal threads of said first internal elongate lumen and said prosthesis guide pin of said prosthesis deployment assembly is said fourth advanced into said second internal elongate lumen of said prosthesis;

i. advancing said prosthesis into said pilot SI joint opening with said prosthesis deployment assembly;

j. disengaging said prosthesis deployment assembly from said prosthesis; and k. withdrawing said prosthesis deployment assembly out of said dysfunctional SI joint.

2. The method of claim 1, wherein said method further comprises the step of providing an image capture apparatus adapted to capture images of said elongated guide probe and said defect creation assembly when positioned proximate to and in said dysfunctional SI joint.

3. The method of claim 2, wherein said image capture apparatus is selected from the group consisting of a fluoroscope, a computed tomography (CT) system, an ultrasound system, a radiography system, and a magnetic resonance imaging system.

4. The method of claim 3, wherein said method further comprises the step of determining at least one position and orientation of said elongated guide probe and said defect creation assembly when said elongated guide probe and said defect creation assembly are positioned proximate to and in said dysfunctional SI joint by intraoperatively capturing images of said elongated guide probe and said defect creation assembly relative to said sacrum bone structure and said ilium bone structure with said image capture apparatus.

5. The method of claim 1, wherein said method further comprises the step of inserting a biologically active composition in at least one of said first and second internal elongate lumens of said prosthesis after said step of said withdrawing of said prosthesis deployment assembly out of said dysfunctional SI joint.

6. The method of claim 5, wherein said biologically active composition comprises a biologically active agent selected from the group consisting of demineralized bone matrix, autograft bone material, allograft bone material, xenograft bone material, polymethyl-methacrylate, calcium-based bone void filler material, including hydroxyapatite (HA) and tricalcium phosphate.

7. The method of claim 5, wherein said biologically active composition comprises a bone morphogenic protein (BMP) composition selected from the group consisting of BMP-1, BMP2a, BMP2b, BMP3, BMP4, BMP5, BMP6, BMP7 and BMP8a.

* * * * *